United States Patent
Schliehe-Diecks et al.

(10) Patent No.: US 10,726,941 B2
(45) Date of Patent: Jul. 28, 2020

(54) METHODS AND SYSTEMS FOR PREDICTING ALLOREACTIVITY IN TRANSPLANTATION

(71) Applicants: Pirche AG, Berlin (DE); UMC Utrecht Holding B.V., Utrecht (NL)

(72) Inventors: Ralf Schliehe-Diecks, Hoppegarten (DE); Hendrikus Theodorus Spierings, EG Zeist (NL)

(73) Assignees: PIRCHE AG, Berlin (DE); UMC UTRECHT HOLDING B.V., Utrecht (NL)

( * ) Notice: Subject to any disclaimer, the term of this patent is extended or adjusted under 35 U.S.C. 154(b) by 310 days.

(21) Appl. No.: 15/309,211

(22) PCT Filed: Apr. 22, 2015

(86) PCT No.: PCT/EP2015/058708
§ 371 (c)(1),
(2) Date: Nov. 7, 2016

(87) PCT Pub. No.: WO2015/169597
PCT Pub. Date: Nov. 12, 2015

(65) Prior Publication Data
US 2018/0189443 A1 Jul. 5, 2018

Related U.S. Application Data

(60) Provisional application No. 61/989,728, filed on May 7, 2014.

(30) Foreign Application Priority Data

May 7, 2014 (EP) .................................... 14167392

(51) Int. Cl.
*G16B 20/00* (2019.01)
*G01N 33/68* (2006.01)
*G01N 33/569* (2006.01)
*G16B 99/00* (2019.01)
*G16B 20/30* (2019.01)

(52) U.S. Cl.
CPC ....... *G16B 20/00* (2019.02); *G01N 33/56977* (2013.01); *G01N 33/6878* (2013.01); *G16B 20/30* (2019.02); *G16B 99/00* (2019.02); *G01N 2333/70539* (2013.01); *G01N 2800/245* (2013.01)

(58) Field of Classification Search
None
See application file for complete search history.

(56) References Cited

FOREIGN PATENT DOCUMENTS

| | | |
|---|---|---|
| CN | 1482563 A | 3/2004 |
| WO | 02069198 A2 | 9/2002 |
| WO | 2007056825 A1 | 5/2007 |
| WO | 2007124578 A1 | 11/2007 |

OTHER PUBLICATIONS

Eckman et al. IBM J. Res. & Dev. vol. 50 No. 6, 2006, 545-560.*
Duquesnoy et al., Retransplant candidates have donor-specific antibodies that react with structurally defined HLA-DR,DQ,DP epitopes. Transpl Immunol. 18(4) (Feb. 2008), pp. 352-360.
Geneugelijk et al., Predicting Alloreactivity in Transplantation, Journal of Immunology Research, vol. 32, No. 9, (Jan. 1, 2014), pp. 2510-2512.
Hammer et al., Precise prediction of major histocompatibility complex class II-peptide interaction based on peptide side chain scanning. J Exp Med. Vo. 180 (1994), pp. 2353-2358.
Otten et al., Predicted indirectly recognizable HLA epitopes presented by HLA-DR correlate with the de novo development of donor-specific HLA IgG antibodies after kidney transplantation, Human Immunology 74 (Mar. 1, 2013), pp. 290-296.
PCT/EP2015/058708: Written Opinion dated Nov. 12, 2015.
Silva et al., Evaluation of HLA Matchmaker compatibility as predictor of graft survival and presence of Anti-HLA antibodies. Transplant Proc. 42(1) (2010), pp. 266-269.

* cited by examiner

*Primary Examiner* — Michael L Borin
(74) *Attorney, Agent, or Firm* — Agris & Von Natzmer, LLP; Joyce von Natzmer

(57) ABSTRACT

The invention relates to a method, system and/or data structure for carrying out a computer implemented method for determining the numbers of predicted indirectly recognized HLA epitopes (PIRCHES) between one or more donors and one or more recipients of transplantation material. The method, system and data structure described herein allow the identification of permissible mismatches and therefore relatively safe transplantation material by analyzing via a computer implemented method HLA-derived peptides of patient and donor.

Figure 1:
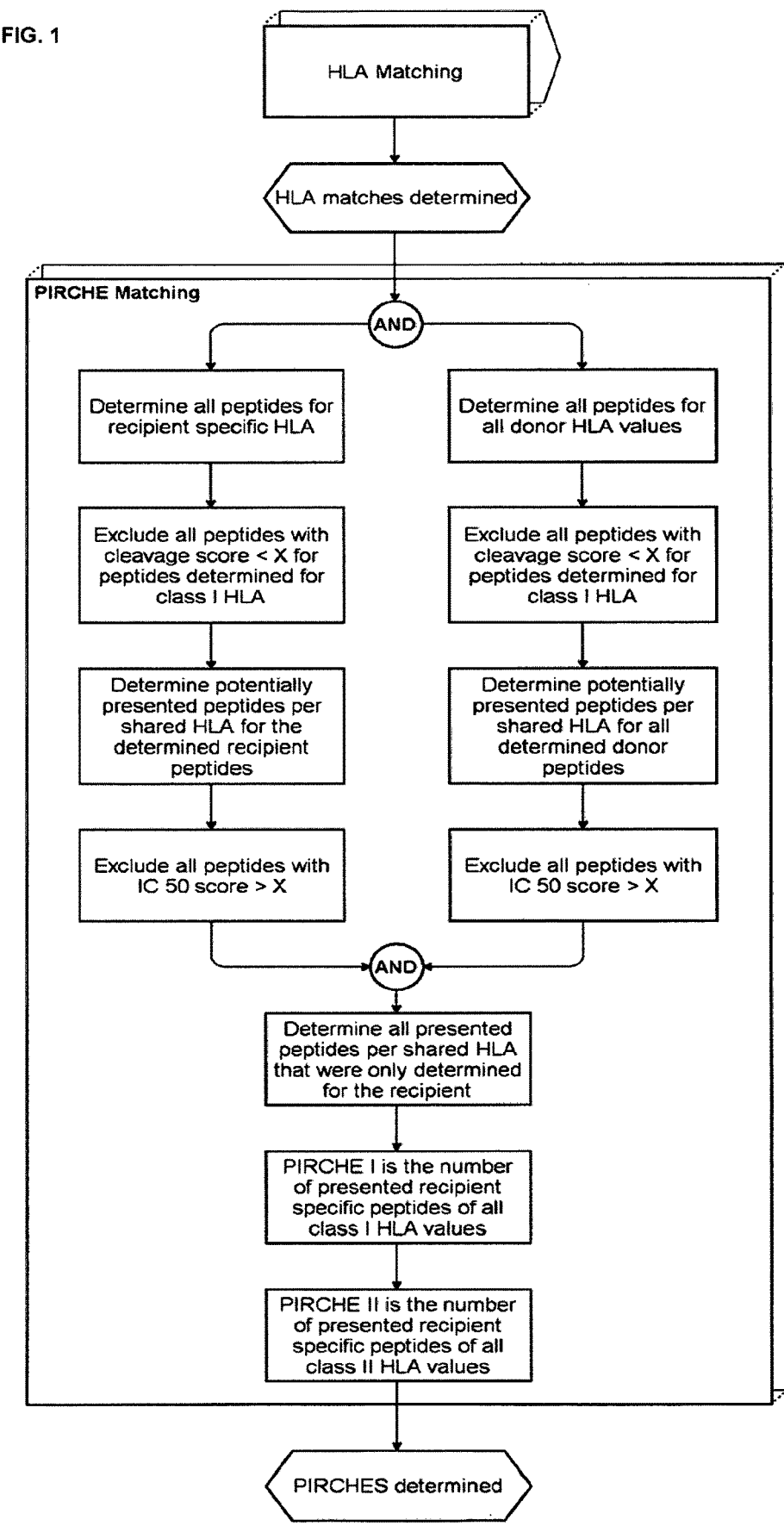

17 Claims, 7 Drawing Sheets
Specification includes a Sequence Listing.

Fig. 5 (cont.)

Legend:

1. Cleavage Threshold
2. IC 50 Score Threshold
3. Matching Direction
4. Patient ID
5. Donor ID
6. Mismatched Patient HLA
7. Mismatched Donor HLA
8. Shared HLA
9. PIRCHE I
10. PIRCHE II
11. HLA Value
12. PIRCHE Value
13. HLA Value Set
14. HLA Value Set Peptides
15. HLA Value Presented Peptides
16. Patient Presented Peptides
17. Donor Presented Peptides
18. PIRCHE Value
19. Patient/Donor HLA Value Set ID

METHODS AND SYSTEMS FOR PREDICTING ALLOREACTIVITY IN TRANSPLANTATION

CROSS-REFERENCE TO RELATED APPLICATIONS

This is the U.S. national stage of International application PCT/EP2015/058708, filed Apr. 22, 2015 designating the United States and claiming priority to European application no. EP 14167392.1, filed May 7, 2014 and the benefit of U.S. application No. 61/989,728, filed May 7, 2014.

INCORPORATION OF SEQUENCE LISTING

The sequence listing was filed as a text file as part of International application PCT/EP2015/058708, filed Apr. 22, 2015 is hereby incorporated by reference. An extra copy of this text file named "eolf-seql.txt", which is 1.8 kilobytes (measured in MS-WINDOWS), dated Nov. 6, 2016 was downloaded from WIPO and was submitted on Nov. 7, 2016 via the USPTO EFS system.

The invention relates to a method, system and/or data structure for carrying out a computer implemented method for determining the numbers of predicted indirectly recognized HLA epitopes (PIRCHES) between one or more donors and one or more recipients of transplantation material. The method, system and data structure described herein allow the identification of permissible mismatches and therefore provision of relatively safe transplantation material via in silico analysis of HLA-derived peptides of patient and donor.

This invention therefore relates to practical embodiments of a computer-implemented method that electronically simulates biological phenomena in a novel data structure or data source in a fast and reliable method. The novel data structure enables the development of interactive software modules that determine of the number of recipient- or donor-specific HLA-derived peptides from a mismatched recipient-HLA allele that are predicted to be presented by a shared (matched) HLA molecule (PIRCHES). Large numbers of PIRCHES are associated with an increased risk of an unwanted immune reaction after transplantation of donor material. The prediction of the numbers of PIRCHES in a fast and efficient manner therefore enables an improved selection of safe transplantation material. Furthermore, the invention specifies how the functionality shall be integrated in existing HLA matching (for example CordMatch) applications.

BACKGROUND OF THE INVENTION

Transplantation of allogeneic cells, tissues and organs is an evolving therapy that has become an increasingly attractive therapeutic option. The number of patients receiving transplants from unrelated donors is expected to double in the near future. Alloreactivity after transplantation has a major impact on clinical outcome, with pathological as well as beneficial effects. HLA mismatches are known to induce an immune reaction after transplantation, however the factors involved in predicting risk of unwanted immune reaction are not well understood.

Hematopoietic Stem Cell Transplantation (HSCT) is one example of a quickly growing therapeutic approach. The major limiting factor of HSCT remains the risk of graft-versus-host disease (GVHD), and since the number of patients receiving HSCT is expected to increase, the provision of novel approaches to prevent GVHD must be accelerated. To overcome the risk of GVHD, patients are preferably transplanted with a donor that is completely matched for all HLA-alleles. However, due to diversity of HLA molecules in the population, these completely matched donors are not available for approximately 40% of patients. When a completely matched donor is not available, a clinician often has to face the difficult decision to choose the best donor out of the mismatched donors (i.e. the one that carries the lowest GVHD risk).

Until now, determining which donor is most suitable relies on a laborious assay that requires up to 14 days of lab-work, for example the cytotoxic T-lymphocyte precursor frequency (CTLpf) assay. Functionally, better-permissible mismatches can be determined with the CTLpf assay. CTLpf scores of less than or equal to 1 per $10^6$ PBL is associated with a better overall survival (Heemskerk et al (2007) Bone Marrow Transplantation, 40, 193-200). Despite such useful information able to be provided by laboratory methods, the time required for the analysis is prolonged and may lead to further detriment or death in patients in need of transplantation. Similar problems face clinicians before selecting transplantation material for cord blood or cord blood cell transplantations, kidney transplantations, or other transplantations at risk of side effects caused by unwanted alloreactivity. To find an alternative for the CTLpf assay, multiple, so far unsuccessful, attempts have been undertaken to predict non-permissible mismatches using two generally available prediction programs, HLAMatchmaker and HistoCheck.

HLAMatchmaker determines potential epitopes for antibodies and has proven its validity for solid-organ transplantation (Duquesnoy et al, Hum. Immunol. 2002; 63: 353-63; Duquesnoy et al, Transplantation 2003; 75: 884-89). HLA-Matchmaker considers differences in amino-acid triplets as epitopes on HLA. Although antibodies potentially play a role in the development of GVHD, predictions based on HLAMatchmaker are not correlated to alloreactivity (Gupta et al, Blood 2010; 116: 1839-48).

HistoCheck is based on the concept of direct recognition of HLA disparities, that is, donor T cells recognize an intact mis-matched-HLA molecule loaded with a non-polymorphic peptide (Amir et al, Blood 2011; 118: 6733). HistoCheck determines the structural differences in HLA molecules in the peptide-binding grooves or regions contacting the T-cell receptor (Elsner et al, Bone Marrow Transplant. 2004; 33:165-69). By determining these structural differences, it aims to predict the likelihood of direct recognition of HLA disparities. Dissimilarity scores obtained with HistoCheck are also not correlated to alloreactivity (Spellman et al, Biol. Blood Marrow Transplant, 2011; Askar et al, Biol. Blood Marrow Transplant. 2011; 17: 1409-15).

In light of the previously existing techniques there exists a need for more reliable and faster methods for predicting whether donor material for a transplantation, which is HLA mismatched, is at increased risk of leading to a failed transplantation, for example development of GVHD, and/or an increase in mortality.

SUMMARY OF THE INVENTION

In light of the prior art the technical problem underlying the present invention is the provision of improved or alternative computer-implemented means for the selection of donor cells or tissue preparations suitable for allogeneic transplantation with a low risk of adverse reaction, or for the prediction of an unwanted immune response in patients undergoing transplantation procedures, in particular via the determination of the number of PIRCHES between any given donor and recipient pair.

This problem is solved by the features of the independent claims. Preferred embodiments of the present invention are provided by the dependent claims.

The invention therefore relates to a computer implemented method for determining the numbers of predicted indirectly recognized HLA epitopes (PIRCHES) between one or more donors and one or more recipients of transplantation material, wherein said PIRCHES are recipient- or donor-specific HLA-derived peptides from a mismatched recipient-HLA allele and are predicted to be presented by a shared (matched) HLA molecule, wherein said method comprises a) Identification of peptides from mismatched HLA molecules of the recipient;
b) Determination of the peptides identified in a) that are predicted to be presented by one or more of the selected shared (matched) HLA molecules;
c) Identification of peptides from all selected HLA molecules of the donor;
d) Determination of the peptides identified in c) that are predicted to be presented by one or more of the selected shared (matched) HLA molecules;
wherein
e) for each shared MHC Class I HLA molecule, any peptide determined in b) that is not included in the set of peptides in d) is characterized as a PIRCHE I, or for each shared MHC Class II HLA molecule, any peptide determined in b) that is not included in the set of peptides in d) is characterized as a PIRCHE II;
characterised in that
f) steps a) to d) are performed on information stored in a graph data structure.

The invention therefore relates to a graph data structure as described herein as such, in addition to its use in a method for determining the number of PIRCHES in any given corresponding method. The data structure may be used in any method step of the invention described herein, as is required or desired. The invention also relates to computer software for execution of the method and/or running of the system as described herein. In one embodiment the method as described herein is characterised in that step f) is carried out by software, for example one or more software modules.

A further embodiment of the invention relates to a system for selecting and/or screening donor material for transplantation, for example for selecting donor material with permissible mismatches from HLA mismatched unrelated donors, comprising software modules for HLA matching, and PIRCHE matching according to the method as described herein.

In one embodiment the method as described herein is characterised in that the information stored in the graph data structure is an electronically-stored representation of biological data, or corresponds to, or is an abstraction of, one or more biological entities. The present invention therefore relates to a computer implemented method in which data are processed that correspond to "real-world" biological entities. The graph data structure as such is not only characterized by the particular architecture of the data structure, but preferably also by the particular biological context of the entities and relationships embodied by the structure.

The novel graph data structure of the invention and its use in the method described herein enables significantly improved (shortened) processing times in comparison to those approaches attempted previously. It was entirely suprising tha the analysis of PIRCHE between donor and recipient could be enhanced to such a significant extent through the data structure employed in the present invention.

In one embodiment the method as described herein is characterised in that HLA matching between donor and recipient has been conducted in advance of carrying out the method described herein. The HLA-typing data of the method may have been carried out in advance and the data regarding HLA-type subsequently analysed via the method of the present invention.

In one embodiment the method as described herein is characterised in that the peptides from mismatched HLA molecules of the recipient and the peptides from HLA molecules of the donor are identified by a computer-implemented method for predicting the cleavage sites of the human proteasome within said HLA molecule(s). This refers preferably to steps a) and c) of the method described herein. The cleavage sites relate therefore preferably to endopeptidase and/or protease sites recognised by the human proteasome. A preferred embodiment of this feature of the invention relates to the use of the software NetChop, or alternative software as described herein, which is capable of determining proteasome cleavage of peptide sequences.

In one embodiment the method as described herein is characterised in that steps b) and d) of claim 1 are performed using a computer-implemented method for predicting the binding of said peptide to any given HLA molecule. A preferred embodiment of this feature of the invention relates to the use of the software NetMHCpan and/or NetMHCII, or other alternatives as described herein, which are capable of determining (or predicting) the binding of any given, preferably nonameric, peptide in HLA or MHC molecules.

Other binding criteria may be applied for predicting whether a peptide will be presented by the HLA molecule. The provided values are based upon binding properties previously described in the literature, but different values may be derived or applied, if the PIRCHE can be reasonably be considered to bind the presenting HLA. The preferred values mentioned herein work surprisingly well. For each donor-recipient pair, presentable recipient- or donor-specific HLA-derived peptides (PIRCHES) are identified.

In one embodiment, per presenting shared-HLA allele, predicted binders derived from donor-HLA alleles are regarded as donor-self peptides, and recipient-HLA alleles regarded as recipient-self peptides, depending on the therapeutic setting, and thus excluded from the analyses. In general, for each donor-recipient pair, the number of presentable recipient- or donor-specific peptides (derived from the mismatched recipient-HLA allele and predicted to be presented by shared HLA) is counted in order to generate the number of PIRCHES.

PIRCHE-I may preferably be identified in two steps:
1) In silico assessment of predicted processing of the amino acid sequences by the proteasome and transportation via the TAP channel is carried out, preferably using NetChop. NetChop is a commonly known software-based method for identifying the cleavage sites of the human proteasome based on sequence analysis. Nonameric peptides are preferably included in the analyses. In a preferred embodiment, the C-terminal cleavage potential is determined. The entire HLA protein is cleaved (in silico) and all positions that are cleavable are marked. From the marked positions backwards, preferably nonameric peptides are identified that are analysed for binding to class I.

As alternatives to NetChop a variety of software-based approaches are known in the art that could be applied, such as MAPP, PaProc or those methods described in Lu et al (J Zhejiang Univ Sci B, 2013 September; 14(9):816-28) or Ginodi et al (Bioinformatics, 2008 Feb. 15; 24(4):477-83).

2) Subsequently, peptides with a high probability of being processed (according to step 1) are tested for their capacity to be presented by HLA that are shared (matched) between the donor and recipient (preferably HLA-A, -B and -C) using NetMHCpan. NetMHCpan is a commonly known method for identifying and/or predicting the binding of peptides to any known MHC molecule using artificial neural networks. The method is trained on more than 150,000 quantitative binding data covering more than 150 different MHC molecules. Predictions can be made for HLA-A, B, C, E and G alleles. The prediction values can be given in nM 1050 values, or as %-Rank to a set of 200000 random natural peptides. Preferably peptides with 1050 binding values <500 nM are chosen as relevant binders.

PIRCHE-II may be identified as follows:

Preferably nonameric binding cores of potential 15-meric HLA-DR, -DQ, and -DP binders may preferably be analysed with NetMHCIIPan 2.0, NetMHCII 1-0, or NetMHCII 2.2. NetMHCII is a commonly known method for predicting binding of peptides to HLA-DR, HLA-DQ, HLA-DP and mouse MHC class II alleles using artificial neuron networks. Predictions can be obtained for 14 HLA-DR alleles covering the 9 HLA-DR supertypes, six HLA-DQ, six HLA-DP, and two mouse H2 class II alleles. The prediction values are given in nM IC50 values, and as a %-Rank to a set of 1000000 random natural peptides. Peptides with IC50-binding values <1000 nM are considered as relevant.

There are a number of alternative methods known in the art, which could be used for determination of HLA binding. SYFPEITHI (based on methods described in Rammensee et al. Immunogenetics 41, 178-228, 1995 and Rammensee et al, Landes Bioscience 1997) and BIMAS are well-known alternatives and are appropriate for class I binding but show some drawbacks in class II binding. Other alternatives relate to Tepitope (based on Stur-niolo et al, 1999, Nat. Biotechnol. 17:555-561), TepitopePAN, EpicCapo, PAAQD, POPI, Propred and Multipred.

In one embodiment the present invention relates to a method as described herein, wherein PIRCHE-I peptides have a predicted IC50 binding value of <10 µM, preferably <1000 nM, more preferably <500 nM.

In one embodiment the present invention relates to a method as described herein, wherein PIRCHE-II peptides have a predicted IC50 binding value of <20 µM, preferably <5 µM, more preferably <1000 nM.

The identification of HLA-derived peptides and their potential binding properties as described above are subsequently provided and/or analysed in the context of a graph data structure.

According to the present invention, and in computer science, the term "graph data structure" is a data type or structure that comprises a collection of nodes (also called vertices), and the connections between them, called edges. A graph data structure may associate to each edge some edge value, such as a numerical attribute.

According to the present invention the nodes of the data structure are preferably represented as HLA value entities and peptide entities, wherein the edges are preferably represented as relationships between HLA value and peptide entities.

Typical operations associated with graph data structures include "adjacent(G, x, y)", which tests whether there is an edge from node x to node y, "neighbors(G, x)", which lists all nodes y such that there is an edge from x to y, or "get_node_value(G, x)", which returns the value associated with the node x. Further operations are available and are capable, for example, of selecting or providing particular nodes defined by certain relationships as defined herein, for example when selecting those peptides to be considered as PIRCHES for any given donor-recipient pair. A skilled person is therefore capable of using a graph data structure as described herein, via various operations carried out in software programmes, in order to determine the desired information regarding the number of PIRCHES for any given donor-recipient pair.

In one embodiment the method, or the graph data structure as such, as described herein is characterised in that the graph data structure comprises:
one or more HLA value entities,
one or more peptide entities, and
one or more relationships between said HLA value and peptide entities, wherein each entity is present in a single instance within the graph data structure and may exhibit one or more relationships to another entity.

In a preferred embodiment the one or more HLA value entities relate preferably to an informational and/or computational representation of an HLA allele. In a preferred embodiment the HLA value entities relate to alleles that are defined by a unique protein sequence, whereby HLA alleles that show only DNA sequence differences without changes in the corresponding protein sequence are preferably not considered in the method. An example of such HLA alleles that show only DNA sequence differences relate to allele-specific features described in fields 3 and 4 of the standard HLA nomenclature system relating to synonymous DNA sequence changes or sequence changes outside a coding region.

In a preferred embodiment the one or more peptide entities relate preferably to an informational and/or computational representation of a peptide sequence derived from an HLA value entity, whereby the sequence of any given HLA allele may be cleaved via a computational approach to produce a peptide sequence of any given length from within the HLA protein sequence, wherein peptides are preferably 5 to 30, preferably 7 to 11, more preferably 9, or preferably 12 to 18, more preferably 15, amino acids in length.

In one embodiment the method, or the graph data structure as such, as described herein is characterised in that HLA value entities have relationships to peptides, but not to other HLA entities, and peptides have relationships to HLA values, but not to other peptides. Through this set of relationships a graph data structure is formed that enables efficient (fast) interrogation.

In one embodiment the method, or the graph data structure as such, as described herein is characterised in that any given HLA value entity "has" a number of peptides (from 1 to n), wherein each peptide of (derived from) any given HLA value entity has a relationship to said HLA value entity. The graph data structure is therefore defined by the relationships between each HLA value entity to its connected peptide entities, said relationships being preferably defined by the predicted proteasome cleavage of the amino acid sequence of the corresponding HLA molecule and the likelihood of proteasome cleavage.

In one embodiment the method, or the graph data structure as such, as described herein is characterised in that the peptides (and number thereof) of each HLA value entity are determined by the predicted proteasome cleavage of the amino acid sequence of the corresponding HLA molecule.

In one embodiment the method, or the graph data structure as such, as described herein is characterised in that the likelihood of proteasome cleavage is expressed by the cleavage score from 0 to 1 (preferably between 0 and 1), wherein said score represents a property of the relationship between any given HLA value entity and peptide entity.

In a preferred embodiment the method, or the graph data structure as such, as described herein is characterised in that steps a) and c) of claim 1 are carried out so that said identification of peptides is determined according to the cleavage score. In one embodiment a cleavage score (relationship property or attribute) of preferably >0.5 (threshold may be from 0 to 1, preferably between 0.1 to 0.9, more preferably between 0.3 to 0.7, most preferably 0.5) for any given peptide is sufficient for peptide identification for said HLA molecule.

In one embodiment the method, or the graph data structure as such, as described herein is characterised in that any given HLA value entity "presents" a number of peptides (from 0 to n), wherein each peptide presented by any given HLA value entity has a relationship to said HLA value entity.

In one embodiment the method, or the graph data structure as such, as described herein is characterised in that the presentation of a peptide by an HLA value entity is determined by the predicted binding and presentation of said peptide by said HLA molecule.

In a preferred embodiment the likelihood of peptide presentation (such as predicted binding of said peptide and presentation on cell surface) is expressed by the IC 50 score, which represents a property of a relationship between any given HLA value entity and peptide entity. In one embodiment for steps b) and d) of claim 1 said determination of peptides is carried out using an IC 50 score threshold.

In one embodiment the method, or the graph data structure as such, as described herein is characterised in that said threshold is preferably an IC 50 score of 5500 for PIRCHE I and/or 51000 for PIRCHE II, wherein such scores are sufficient for determination of predicted presentation of said peptide.

In a preferred embodiment the selected HLA molecules are the HLA loci A*, B*, C*, DRB1* and DQB1*, and optionally DPB1* and DRB3/4/5*.

A further aspect of the invention relates to a system for selecting and/or screening donor material for transplantation, for example for selecting donor material with permissible mismatches from mismatched unrelated donors, comprising software modules for HLA matching, and PIRCHE matching according to the method of the preceding claims.

In a preferred embodiment the system for selecting and/or screening donor material for transplantation is characterised in that said HLA software module carries out HLA matching between donor and recipient HLA typing data on the basis of high resolution allele coding (e.g. A*02:01), preferably for HLA loci A*, B*, C*, DRB1* and DQB1*, and optionally DPB1* and DRB3/4/5*.

It is further preferred that said PIRCHE matching incorporates the HLA matching information generated by said HLA matching software module, such that the PIRCHE matching module preferably accepts a patient, a matching profile and list of HLA matched donors and preferably cord blood units (CBUs) and returns the input donor list enriched with the PIRCHE information to the service client.

In a preferred embodiment the system is characterized in that patient information and search profiles are provided via a shared service integration manager software module, wherein said shared service integration manager module is connected to both HLA matching and PIRCHE matching modules, such that patient information and search profiles are initially processed by said HLA matching software module, which subsequently provides a patient, a matching profile and list of HLA matched donors and preferably cord blood units (CBUs) via said shared manager module for analysis of PIRCHE numbers to said PIRCHE matching module.

The various embodiments of the system provide combined approaches towards HLA matching and PIRCHE matching, thereby providing a unique service to transplantation providers searching for transplantation material with low risk of causing unwanted allogenic reactions. The technical effect of the system described herein is not only the improved speed of interrogation of donor databanks, but also the provision of safer transplantation material, thereby increasing health of the patient population having received transplantations of allogenic material.

In one aspect of the invention the method or system as described herein is characterised in that the information corresponding to donor HLA value entities is obtained from one or more donor profiles. The donor profile may be termed as a "donor type", which relates to an electronic (theoretical or according to a real donor) representation of any given potential combination of HLA alleles, and/or haplotypes, that may occur in an individual subject. A donor profile or type is preferably stored in an additional data structure, database, library and/or simulation comprising all possible donor types as described above.

In a preferred embodiment the donor profiles are preferably stored in an additional data structure, database, library and/or simulation of the peptide and/or HLA value entities of any given one or more theoretical or virtual donors. In one embodiment preferably multiple donor profiles or donor types are stored in a donor data structure, database, library and/or simulation comprising preferably essentially all possible donors for essentially all possible genotypes or possible combinations of HLA alleles, and/or haplotypes.

The phrase "essentially all" relates in this context to a significant number of, preferably all, or every known, protein variant of the allele group. The method therefore can effectively determine whether a particular donor or allele group indeed is associated with a relatively low PIRCHE value and therefore present itself as a preferred selection. Because those skilled in the art are able to make a pre-selection of possible protein variants within any given allele group, either on the basis of the reliability of the stored data or on population frequencies of certain alleles, the method is not limited to analysis of all known protein sequences of an allele group. In one embodiment the method will encompass the analysis of essentially all known (or relevant) protein sequences within the allele group, in order to provide more definitive results.

In a preferred embodiment of this aspect the method or system of the invention is characterised in that said method and/or system enables searching with recipient information (corresponding preferably to a biological recipient in need of a transplantation) against one or more donor profiles, wherein the result (outcome) of said system and/or method provides information on the one or more (preferably multiple) best-matched mismatched donor profiles, preferably a 9/10 mismatched donor with a lowest possible number of PIRCHES.

In one embodiment the method or system of the invention is characterised in that said method and/or system is functionally connected to electronic registers of donor material (for example registers that do not have information stored on PIRCHES), wherein the outcome of the method and/or system of the preceding claim enables a query to be sent from an end-user of said method and/or system to said register for any given one or more best-matched mismatched donor material corresponding to said outcome. The invention preferably links the end user, for example a medical practitioner or transplant provider, with the stem cell or other donor material registers that comprise information on said donor material.

In one embodiment the method or system of the invention is characterised in that information representing the frequency of any given combination of HLA alleles (known for example as a haplotype or genotype) in any one or more human populations (such as age, gender, ethnicity, etc. . . . ) is incorporated in said profile for each potential HLA allele combination of the donor profile.

In one embodiment the method or system of the invention is characterised in that electronically stored HLA typing data for donor material typed with "low-" or "medium-" resolution HLA typing is converted via a computer-implemented method into a "high-" resolution-similar or analogous HLA typing status on the basis of the known population frequencies of any given combination of HLA alleles determined by said with "low-" or "medium-" resolution HLA typing, thereby enabling interrogation of HLA typing data previously obtained via "low-" or "medium-" resolution techniques using the method and/or system as described herein.

A large number of donor samples stored for transplantation are at present only typed at either "low" or "intermediate" resolution. When no completely matched donor material is evident, some of the mismatched donor material may also be suitable for transplantation. However, clinicians searching for matched donor material face a difficult task in selecting "low" or "intermediate" resolution typed material for transplantation, or for further high resolution typing before transplantation. Determining which donor is most likely to provide acceptable allogeneic material, or which mismatched allele group is most likely to be associated with a low risk of an adverse immune reaction, remains a challenge for clinicians when faced with "low" or "intermediate" resolution typed donor information. The present invention therefore enables conversion of "low-" or "medium-" resolution HLA typing to "high" resolution data.

Considering the enormous health cost to patients having suffered from unwanted immune responses after transplantation, in addition to relatively high costs for carrying out high resolution typing, methods for the prediction of safely transplantable material and for the prediction of which mismatched or potentially mismatched donors are associated with a lower risk of an unwanted immune reaction, are of paramount importance to the medical community. The method as described herein enables reduction of risk upstream of surgery (or treatment) and upstream of any high resolution typing that may be required, thereby avoiding substantial health and financial cost to patients, medical practitioners and institutions, respectively.

In one embodiment the method or system of the invention is characterised in that said method and/or system comprises a) conversion of HLA typing data (of preferably donors) from "low-" or "medium-" resolution HLA typing to "high-" resolution data, b) HLA matching of said donor information with recipient HLA information and c) PIRCHE matching according to the method and/or system described herein.

A further aspect of the invention relates to a method or system characterised in that information representing the frequency of any given combination of HLA alleles (known for example as a haplotype or genotype) in any one or more human populations (such as age, gender, ethnicity, etc. . . . ) is incorporated in said profile for each potential HLA allele combination of the donor profile, wherein preferably electronically stored HLA typing data for donor material typed with "low-" or "medium-" resolution HLA typing is converted via a computer-implemented method into a "high-" resolution-similar or analogous HLA typing status on the basis of the known population frequencies of any given combination of HLA alleles determined by said with "low-" or "medium-" resolution HLA typing, thereby enabling interrogation of HLA typing data previously obtained via "low-" or "medium-" resolution techniques using the method and/or system as described herein.

The transplantation material may relate to any given biological matter intended for transplantation. Such biological matter may relate to cells, tissue, blood, in particular cord blood, hematopoietic stem cells, or other progenitor or stem cell populations, or organs for transplantation.

The computer implementation of the invention enables an efficient, fast and reliable method for identification of potentially permissible donor material for allogeneic transplantation. The data processed by the software can be handled in a completely or partially automatic manner, thereby enabling in a preferred embodiment an automated computer-implemented method. Data regarding the HLA typing of donor and recipient, in addition to the number of PIRCHES determined for any donor-recipient pair, can be stored electronically and eventually maintained in appropriate databases. The invention therefore also relates to computer software capable of carrying out the method as described herein. The invention further relates to a preferably automated computer-implemented method for prediction of an immune response against human leukocyte antigens (HLA) after transplantation, wherein the number of PIRCHES is correlated with risk of an unwanted immune reaction.

The system preferably comprises one or more databases with information on all published HLA alleles. The database may be updated as new HLA allele sequences are published. Computer software, which could also be based on any given computing language, can be used for generating and/or updating the databases, in addition to calling the respective programmes required.

The invention further comprises a system for preferably pre-transplantation prediction of an immune response against human leukocyte antigens (HLA), which may occur after transplantation. The system may comprise computing devices, data storage devices and/or appropriate software, for example individual software modules, which interact with each other to carry out the method as described herein.

In one embodiment the system may comprise databanks or databases of a cord blood bank, whereby each sample is tested for HLA-type, and the information stored electronically. The system may also comprise a connection between an additional computing device, for example a device of a clinician, transplant centre, or hospital, in which the HLA-type data for the recipient is stored. Through a connection between the multiple databases, for example over the internet, the method of the invention can be carried out using appropriate software. HLA-types of multiple potential donor samples and the patient may be compared and the number of PIRCHE for any given donor-recipient pair determined. In light of the analysis based on the method described herein a clinically relevant prediction can be made whether any given donor material, for example those samples stored in a cord blood bank or other cell or tissue bank, is suitable for transplantation.

In one embodiment the present invention relates to a method as described herein, wherein HLA typing is carried out on HLA subtypes HLA-A, HLA-B, HLA-C, HLA-DRB1, HLA-DQB1, HLA-DPB1, -DQA1, -DPA1, -G, -E, -F, MICA, MICB and/or KIR.

In one embodiment the present invention relates to a method as described herein, wherein HLA typing is carried out on HLA-A, -B, -C, -DRB1 and -DQB1. These 5 alleles provide the basis for the commonly used terminology "9/10-matched", which refers to a 9/10-matched unrelated donor. In such a case 9 of the 10 alleles of these 5 genes show a match but one remaining allele does not match. The present invention therefore allows, in a preferred embodiment, determination of whether the use of material from such a 9/10-matched unrelated donor is safe, i. e. whether the mismatch is permissible for transplantation.

The invention relates also to the method as described herein for finding permissible HLA-mismatches in donor samples where more mismatches are present than the common 9/10 scenario. One example of potential donors who are encompassed by the present invention are Haploidentical donors, who may be screened using the method described herein for permissible mismatched donor material. A haploidentical related donor, may be described as a donor who has a "50% match" to the patient. This type of donor can be a parent, sibling, or child. By definition, a parent or child of a patient will always be a haploidentical donor since half of the genetic material comes from each parent. There is a 50% chance that a sibling will be a haploidentical donor. Haploidentical HSCT offers many more people the option of HCT as 90% of patients have a haploidentical family member. Other advantages include: immediate donor availability; equivalent access for all patients regardless of ethnic background; ability to select between multiple donors; and ability to obtain additional cells if needed. Alternatively, cord blood units (CBUs) may not show a high level of HLA-matching, but still be suitable for transplantation if the mismatches are permissible as determined by the method as described herein. CBU's are typically minimally 4/6 matched, but this match can however lead to a 4/10 or 5/10 situation at the allelic level.

Considering that the method as described herein relies to some extent on shared HLA, the minimum HLA-match is one allelic match. Although this is unlikely to occur for HSCT, such a scenario will frequently arise for organ transplantation, due to the limited number of donor material available. The invention may therefore be carried out on mismatched samples with a minimum of one allelic match. The mismatched donor may therefore relate to a 1/10, 2/10, 3/10, 4/10, 5/10, 6/10, 7/10, 8/10, 9/10 or 10/10 (DP mismatch) match. If additional alleles are tested, the donor may also show any other kind of mismatch, whereby at least one allelic match is present. Preferred for the transplantation are donors with significant HLA-matches. If additional alleles are subjected to typing the donor could therefore be for example 11/12- or 13/14-matched.

In one embodiment the present invention relates to a method as described herein, wherein HLA typing comprises serological and/or molecular typing. In a preferred embodiment the present invention relates to a method as described herein, wherein HLA typing is carried out at high resolution level with sequence-based typing.

In one embodiment the present invention relates to a method as described herein, wherein HLA typing comprises sequencing of exon 1-7 for HLA class I alleles and exon 1-6 for HLA class II alleles. In one embodiment the present invention relates to a method as described herein, wherein HLA typing comprises high resolution HLA-A, -B, -C, -DRB1 and -DQB1 typing of exons 2 and 3 for HLA class-I alleles and exon 2 for HLA class-II alleles. These particular HLA-typing approaches are described in the examples provided herein and demonstrate advantages over earlier typing methods, providing full coverage of the alleles that need to be typed to identify the mismatches.

DETAILED DESCRIPTION OF THE INVENTION

Historically, alloreactivity after HSCT is considered to be evoked mostly due to direct recognition of HLA disparities by donor T cells. This means that the graft T cells recognize mismatched HLA that is expressed as an intact molecule on the cell surface of host cells. The present invention is however based in particular upon indirect recognition. Alloreactivity can be evoked when peptides derived from the mismatched host HLA allele are processed and presented on shared HLA and thereby recognized by the donor T cells.

Binding of peptides to HLA molecules is predictable. The differences between predicted binding affinities and experimental measurements have been shown to be as small as the differences in measurements between different laboratories. Predictability is particularly high for HLA class-I molecules, as these molecules have a more strict preference for nine amino acid long peptides (9-mers) and require specific amino acids as anchor residues at clearly defined anchor positions. For HLA class II molecules predictability is lower, as peptides of different length can bind using different positions as anchor residues. Therefore, it is difficult to determine how a peptide aligns to the HLA class II-binding groove and which amino-acid residues in the peptide are preferred as anchors. To solve this problem, Nielsen et al. used a so-called core predictor to estimate how a peptide positions in the class II binding groove. The core predictor enabled the development of an accurate HLA class-II predictor, called NetMHCII.

Despite the advances in predicting peptide binding to class I and class II HLA molecules, there is still significant uncertainty in assessing the factors involved in alloreactivity and the production of donor-specific antibodies (DSA). Considering the tools presently available to predict unwanted immune responses after kidney transplantation, there exists a need to provide more reliable methods for assessing potentially adverse reactions in advance of transplantation.

Conceptually, mismatched HLA-directed T-cell alloreactivity may result from direct and indirect recognition of HLA disparities. So far, studies that aimed at explaining and predicting the clinical alloreactivity towards mismatched HLA, mainly focused on direct recognition of HLA disparities. Direct recognition involves donor T cells that recognize an intact mismatched-HLA molecule loaded with a non-polymorphic peptide. When polymorphisms in HLA alleles lead to differences in the peptide-binding groove, the presented peptide repertoire of HLA molecules may differ substantially. These different peptide repertoires may lead to T-cell responses. The HistoCheck algorithm determines structural differences in HLA molecules in the peptide-binding grooves or regions contacting the T-cell receptor, thereby predicting a dissimilarity score. However, the scores obtained with HistoCheck do not correlate with alloreactivity, neither in vitro, nor in vivo.

T-cell related alloreactivity can potentially also be evoked by indirect recognition of the mis-matched-HLA allele. Indirect recognition has been studied in great detail for minor histocompatibility (H) antigens. Mismatches for these HLA-presented polymorphic proteins are associated with an increased risk of aGVHD, and a decreased risk of relapse.

Analogous to peptides derived from minor H mismatches, peptides derived from mismatched-HLA molecules can also be presented by HLA.

Indirect recognition of the mismatched-HLA antigen may lead to T cell-related alloreactivity. During indirect HLA recognition, T cells recognize peptides derived from polymorphic HLA antigens presented by a shared (matched) HLA molecule. Peptides derived from mismatched-HLA molecules are frequently presented by HLA. These indirectly recognizable HLA epitopes have been associated with both acute and chronic graft failure in solid organ transplantation. T cells that indirectly recognize HLA-mismatches in the context of self-HLA may therefore play an important role in clinical alloreactivity.

The present invention therefore designates the HLA-derived epitopes that are predicted to be presented as Predicted Indirectly ReCognizable HLA Epitopes (PIRCHES). The present invention identifies PIRCHES presented by shared-HLA class-I (PIRCHE-I) and class-II (PIRCHE-II) separately. PIRCHE-II are shown to induce alloreactivity after kidney transplantation; PIRCHES presented by HLA-DR correlated with the de novo development of donor-specific HLA IgG antibodies.

The present invention is therefore based on the finding that recognition of HLA-derived peptides has an effect on clinical alloreactivity after HLA-mismatched HSCT. To this end, numbers of predicted PIRCHE-I and -II can be assessed and their role evaluated in the adverse clinical effects of HSCT. On the basis of such investigation, the present invention describes universally applicable methods that can predict non-permissible HLA mismatches prior to HSCT and other cell or organ transplants.

The approaches of the prior art, such as HLAMatchmaker, which assesses the degree of structural compatibility between mismatches, have not provided effective means for predictive determination of the risk of an unwanted immune reaction. HLAMatchmaker considers the structural basis of epitopes on HLA-antigens that could induce HLA-antibodies. It does so by looking at HLA class I antigens as a combination of short sequences (triplets), and determining the differences in these triplets. The degree of triplet mismatching did not significantly correlate to aGVHD. An additional method of the prior art, HistoCheck, the method evaluated by Spellman and Askar and colleagues, rates the amino acid differences between HLA-allelic products based on the position within the HLA molecule and the functional similarity of amino acids within proteins. The Dissimilarity Scores that were obtained with this ranking system did not predict aGVHD.

Since the previous attempts with computational methods were unable to predict GVHD, the method of the present invention represents one of the first computer implemented method that provides improved donor selection for HSCT with a reliable and effective pre-transplantation prediction of an unwanted and potentially dangerous immune response. Furthermore, while the previous attempts were undertaken with approaches that mostly asses the structural/functional dissimilarity between HLA molecules (i.e. are based on direct recognition of HLA disparities or the possibility of recognition via antibodies) the present invention preferably is based on predicted indirect recognition of HLA mismatched molecules. The method of the present invention is surprisingly suitable to predict alloreactivity, which was not possible before. The invention therefore is based on the key principle, that the number of predicted indirectly recognizable HLA epitopes (PIRCHES) correlates with the likelihood of an unwanted immune response post-transplantation.

The present invention therefore represents the technical utilisation of the relationship between risk of alloreactivity and increased numbers of mismatched HLA-derived peptides presented by shared-HLA molecules. These numbers can be determined preferably in silico and can be used as a predictive marker with respect to the development of alloreactivity, for example GVHD.

The present invention provides a preferably computer implemented method that determines which donor is suited for transplantation when a completely matched donor is not available, without the need for laborious compatibility assays. The present invention for example is applicable to multiple transplant settings, such as stem cells, cord blood cells or solid organ transplantation, amongst others. Essentially any transplantation, in which HLA-matching plays a role in determining alloreactivity or tissue rejection after transplantation, is encompassed by the present invention.

Considering the enormous health cost to patients having suffered from unwanted immune responses after transplantation, methods for the prediction of safely transplantable material are of paramount importance to the medical community. The method as described herein enables reduction of risk upstream of surgery (or treatment), thereby avoiding substantial health and financial cost to patients, medical practitioners and institutions, respectively.

In one embodiment the invention therefore relates to a method for prediction of an immune response against human leukocyte antigens (HLA) associated with, preferably induced by, HLA-mismatches between donor and recipient after transplantation, wherein HLA-typing for the donor and recipient is conducted, at preferably high resolution level with sequence based typing, to determine the mismatches, the number of predicted indirectly recognized HLA epitopes (PIRCHES) is identified using computer-implemented methods by determining the presentation and/or binding of peptides derived from mismatched recipient and/or donor HLA alleles, whereby the number of PIRCHES correlates with the likelihood of said immune response.

In one embodiment the present invention relates to a method as described herein, wherein said transplantation comprises haematopoietic stem-cell transplantation (HSCT).

In one embodiment the present invention relates to a method as described herein, wherein said transplantation comprises cord blood or cord blood cell transplantation.

In one embodiment the present invention relates to a method as described herein, wherein said transplantation comprises kidney transplantation.

The method of the present invention may also be applied for prediction of an unwanted immune response in the context of other medical disorders, such as secondary recurrent miscarriage, antibody formation during pregnancy, or for assessing risk before cornea transplantation.

In one embodiment the present invention relates to a method as described herein, wherein said immune response comprises an unwanted alloreactivity.

In one embodiment the present invention relates to a method as described herein, wherein said immune response comprises a T-cell-mediated response (alloreactivity). In one embodiment the present invention relates to a method as described herein, wherein said immune response leads to acute graft versus host disease (aGVHD) or chronic graft versus host disease (cGVHD).

The computer implementation of the invention on the basis of the graph data structure enables an efficient, fast and reliable method for identification of potentially permissible donor material for allogeneic transplantation. The data processed by the software can be handled in a completely or partially automatic manner, thereby enabling in a preferred embodiment an automated computer-implemented method. Data regarding the HLA typing of donor and recipient, in addition to the number of PIRCHES determined for any donor-recipient pair, is stored electronically and maintained in an appropriate graph structure database.

In one embodiment the system may comprise databanks or databases of a cord blood bank, whereby each sample is tested for HLA-type, and the information stored electronically. The system may also comprise a connection between an additional computing device, for example a device of a clinician, transplant centre, or hospital, in which the HLA-type data for the recipient is stored. Through a connection between the two databases, for example over the internet, the method of the invention can be carried out using appropriate software. HLA-types of multiple potential donor samples and the patient may be compared and the number of PIRCHE for any given donor-recipient pair determined. In light of the analysis based on the method described herein a clinically relevant prediction can be made whether any given donor material, for example those samples stored in a cord blood bank or other cell or tissue bank, is suitable for transplantation. The invention also relates to a software suitable for carrying out the method described herein.

According to the present invention, the term "prediction" means a statement about possible events in the future. The term "forecast" may also be used. The "prediction" in the sense of the present invention represents an assessment of the likelihood or risk of an immune response occurring after transplantation. On the basis of the prediction, or risk assessment, valuable information is obtained in advance of a potentially harmful event, which can be used to determine further therapeutic options.

The term "Immune response" in the context of the present invention relates to an immune response as commonly understood by one skilled in the art. An immune response may be understood as a response from a part of the immune system to an antigen that occurs when the antigen is identified as foreign, which preferably subsequently induces the production of antibodies and/or lymphocytes capable of destroying or immobilising the "foreign" antigen or making it harmless. The immune response of the present invention may relate either to a response of the immune system of the recipient against the transplanted material, or an immune response effected by cells of the transplanted cells, tissues, or organs, whereby for example in GVHD T cells of the transplanted material react against and/or attack recipient antigens or tissue. The immune response may be a defence function of the recipient that protects the body against foreign matter, such as foreign tissue, or a reaction of immune cells of the transplanted material against recipient cells or tissue.

The human leukocyte antigen (HLA) system is the major histocompatibility complex (MHC) in humans. The super locus contains a large number of genes related to immune system func-tion in humans. This group of genes resides on chromosome 6, and encodes cell-surface antigen-presenting proteins and has many other functions. The proteins encoded by certain genes are also known as antigens, as a result of their historic discovery as factors in organ transplants. The major HLA antigens are essential elements for immune function. HLAs corresponding to MHC class I (A, B, and C) present peptides from inside the cell (including viral peptides if present). These peptides are produced from digested proteins that are broken down in the proteasomes. In general, these particular peptides are small polymers, about 9 amino acids in length. Foreign antigens attract killer T-cells (also called CD8 positive- or cytotoxic T-cells) that destroy cells. HLAs corresponding to MHC class II (DP, DM, DOA, DOB, DQ, and DR) present antigens from outside of the cell to T-lymphocytes. These particular an-tigens stimulate the multiplication of T-helper cells, which in turn stimulate antibody-producing B-cells to produce antibodies to that specific antigen.

MHC loci are some of the most genetically variable coding loci in mammals, and the human HLA loci are no exception. Most HLA loci show a dozen or more allele-groups for each locus. Six loci have over 100 alleles that have been detected in the human population. Of these, the most variable are HLA-B and HLA-DRB1.

An allele is a variant of the nucleotide (DNA) sequence at a locus, such that each allele differs from all other alleles by at least one (single nucleotide polymorphism, SNP) position. Most of these changes result in a change in the amino acid sequences that result in slight to major functional differences in the protein.

"HLA" refers to the human leukocyte antigen locus on chromosome 6p21, consisting of HLA genes (HLA-A, HLA-B, HLA-C, HLA-DRB1, HLA-DQB1, etc. . . . ) that are used to determine the degree of matching, for example, between a recipient and a donor of a tissue graft. "HLA allele" means a nucleotide sequence within a locus on one of the two parental chromosomes.

"HLA typing" means the identification of an HLA allele of a given locus (HLA-A, HLA-B, HLA-C, HLA-DRB1, HLA-DQB1, etc. . . . ). Samples may be obtained from blood or other body samples from donor and/or recipient, which may subsequently be analysed.

Serotyping (identification of the HLA protein on the surface of cells using antibodies) is the original method of HLA typing and is still used by some centres. Phenotyping relates to the serological approach for typing. This method is limited in its ability to define HLA polymorphism and is associated with a risk of misidentifying the HLA type. Modern molecular methods are more commonly used to genotype an individual. With this strategy, PCR primers specific to a variant region of DNA are used (called PCR SSP). If a product of the right size is found, the assumption is that the HLA allele/allele group has been identified. PCR-SSO may also be used incorporating probe hybridisation. Reviews of technical approaches towards HLA typing are provided in Erlich H, Tissue Antigens, 2012 July; 80(1):1-11 and Dunn P, Int J Immunogenet, 2011 December; 38(6):463-73. Gene sequencing may be applied, and relates to traditional methods, such as Maxam-Gilbert sequencing, Chain-termination methods, advanced methods and de novo sequencing such as shotgun sequencing or bridge PCR, or the so-called "next-generation" methods, such as massively parallel signature sequencing (MPSS), 454 pyrosequencing, Illumina (Solexa) sequencing, SOLID sequencing, or other similar methods.

With respect to HLA typing, samples obtained from the donor themselves and/or from donor material before, during or after isolation/preparation for transplantation, may be used for HLA-typing and subsequent comparison to the HLA-typing data from the recipient. For example, HLA-typing of the donor themselves, for example by analysing a saliva, blood or other bodily fluid sample for HLA information, may occur, and optionally additionally or alternatively, the material obtained from the donor intended for transplantation (donor material) may be analysed for the same and/or complementary HLA type characteristics during HLA-typing.

An "HLA-mismatch" is defined as the identification of different alleles in donor and recipient, which are present at any given loci.

According to the present invention, the term "two-field specific HLA protein typing" relates to the standardised HLA naming system developed in 2010 by the WHO Committee for Factors of the HLA System. According to the HLA naming system, the nomenclature is as follows: HLA-Gene*Field1:Field2:Field3:Field4-Suffix. Gene relates to the HLA locus (A, B, C, DRB1, DQB1, etc. . . . ). Field 1 relates to the allele group. Field 2 relates to the specific HLA protein. Field 3 relates to a synonymous DNA substitution within the coding region. Field 4 is used to show differences in a non-coding regions. The suffix is used to denote particular characteristics in gene expression.

The "two-field" within "two-field specific HLA protein typing" relates to the presence of HLA typing information for Fields 1 and 2 according to the standardized WHO nomenclature used herein. This typing is commonly referred to as "high resolution typing" or "specific HLA protein typing", as the typing provides information on the specific protein sequence relevant for the immune responses dealt with herein.

The term "HLA allele group" typing relates to typing information that is provided for only the HLA gene (locus) and Field1. This typing is commonly referred to as "low resolution" typing. According to the present invention any serotype would be converted to a molecular "low resolution" typing.

The term "intermediate resolution" or "medium resolution" typing relates to some kinds of typing information where the presence of some alleles, or allele strings, have been defined in the patient/donor by the typing method used. The NMDP nomenclature is one method of describing this level of typing. For example A*01:AB relates to alleles 01:01 or 01:02 (01:01/01:02) and the patient/donor is one of these two alleles. The NMDP allele codes are in some cases generic, wherein one code may encompass a number of possible HLA sequences (alleles) at any given HLA locus. Although the donor material may be HLA typed, a number of NMDP codes do not provide information on which specific protein is in fact present at any given HLA locus. This form of typing information is referred to as intermediate resolution typing.

The donor is commonly understood to be an individual or multiple individuals (for example in the case of where multiple samples or preparations, such as cord blood units (CBUs) are required for an effective therapeutically relevant amount of donor material for the transplantation) who provide donor material, or in other words biological material, such as but not limited to cells, tissues, organs, or other bodily parts, fluids and/or preparations, for transplantation in the recipient. References to the donor, or HLA-typing of the donor, may also refer to donor material, or HLA-typing of the donor material, respectively.

The subject recipient of the method is typically a mammal, preferably a human. The recipient is typically a patient suffering from a disorder characterised by the need for transplantation, such as organ failure necessitating a transplant. By the term "organ", it is meant to include any bodily structure or group of cells containing different tissues that are organized to carry out a specific function of the body, for example, the heart, lungs, brain, kidney skin, liver, bone marrow, etc. In one embodiment the graft is an allograft, i.e. the individual and the donor are of the same species. The subject may also suffer from a condition that could be treated by the transplantation of cells, even when the disorder itself is not defined by a lack or loss of function of a particular subset of endogenous cells. Some disorders may be treatable by the transplantation of certain kinds of stem cells, whereby the native or endogenous pool of such cells are not necessarily non-functional in the recipient.

The method of the invention is particularly applicable to patients who are about to receive or are predicted to require a cell, tissue or organ transplant, to predict the likelihood of unwanted immune response, such as origin graft damage or rejection, and/or immune origin damage to non-graft tissue. For example, the patient may be expected to receive a transplant in the next one, two, three, four, five, six, or twelve months. Alternatively, the assay is particularly applicable to individuals who have received a transplant to predict the likelihood of immune origin graft damage or rejection, and/or immune origin damage to non-graft tissue. Post-transplant, the method is particularly applicable to patients who show evidence of chronic organ dysfunction (of the graft organ) or possible graft versus host disease (GVHD), particularly chronic GVHD and particularly in cases wherein the graft is a bone marrow transplant.

Transplantation is the moving of cells, tissue or an organ from one body (donor) to another (recipient or patient), or from a donor site to another location on the patient's own body, or from stored donor material to a recipients body, for the purpose of replacing the recipient's damaged or absent organ, or for the purpose of providing stem cells, other cells, tissues or organs capable of providing a therapeutic effect.

Allogeneic transplantation or Allotransplantation is the transplantation of cells, tissues, or organs, to a recipient from a genetically non-identical donor of the same species. The transplant is called an allograft, allogeneic transplant, or homograft. Most human tissue and organ transplants are allografts. Allografts can either be from a living or cadaveric source. Generally, organs that can be transplanted are the heart, kidneys, liver, lungs, pancreas, intestine, and thymus. Tissues include bones, tendons (both referred to as musculoskeletal grafts), cornea, skin, heart valves, nerves and veins.

The invention also encompasses use of the method in the context of screening organs, cells, or tissues produced via regenerative medicine, for example reconstructed donor material that has been constructed ex vivo and is intended for transplantation. Stem cell technologies enable the production of a number of medically relevant cell types or tissues ex vivo. The present invention could therefore also be applied in screening allogeneic material that has been produced by biotechnological and/or tissue engineering methods for its suitability in transplantation.

The invention encompasses the assessment of risk of an immune reaction, preferably a pre-transplantation risk assessment, whereby any given stem cell may be considered as donor material intended for transplantation. For example, hematopoietic stem cell transplantation (HSCT) is the transplantation of multipotent hematopoietic stem cells, usually derived from bone marrow, peripheral blood, or umbilical cord blood. It is a medical procedure common in the fields of hematology and oncology, most often performed for patients with certain cancers of the blood or bone marrow, such as multiple myeloma or leukemia. In these cases, the re-cipient's immune system is usually destroyed with radiation or chemotherapy before the transplantation. Infection and graft-versus-host disease are major complications of allogenic (also referred to as allogeneic) HSCT.

Stem cells are to be understood as undifferentiated biological cells, that can differentiate into specialized cells and can divide (through mitosis) to produce more stem cells.

Highly plastic adult stem cells are routinely used in medical therapies, for example in bone marrow transplantation. Stem cells can now be artificially grown and transformed (differentiated) into specialized cell types with characteristics consistent with cells of various tissues such as muscles or nerves through cell culture. The potential stem cell transplantation may relate to any given stem cell therapy, whereby a number of stem cell therapies exist. Medical researchers anticipate that adult and embryonic stem cells will soon be able to treat cancer, Type 1 diabetes mellitus, Parkinson's disease, Huntington's disease, Celiac disease, cardiac failure, muscle damage and neurological disorders, and many others.

Also known as somatic stem cells and germline stem cells, stem cells can be found in children, as well as adults. Pluripotent adult stem cells are rare and generally small in number but can be found in a number of tissues including umbilical cord blood. Bone marrow has been found to be one of the rich sources of adult stem cells which have been used in treating several conditions including Spinal cord injury, Liver Cirrhosis, Chronic Limb Ischemia and End-stage heart failure. Adult stem cells may be lineage-restricted (multipotent) and are generally referred to by their tissue origin (mesenchymal stem cell, adipose-derived stem cell, endothelial stem cell, dental pulp stem cell, etc.).

Multipotent stem cells are also found in amniotic fluid. These stem cells are very active, expand extensively without feeders and are not tumorigenic. Amniotic stem cells are multipotent and can differentiate in cells of adipogenic, osteogenic, myogenic, endothelial, hepatic and also neuronal lines. It is possible to collect amniotic stem cells for donors or for autoluguous use.

Cord blood-derived multipotent stem cells display embryonic and hematopoietic characteristics. Phenotypic characterization demonstrates that (CB-SCs) display embryonic cell markers (e.g., transcription factors OCT-4 and Nanog, stage-specific embryonic antigen (SSEA)-3, and SSEA-4) and leukocyte common antigen CD45, but that they can be negative for blood cell lineage markers. Additionally, CB-SCs display very low immunogenicity as indicated by expression of a very low level of major histocompatibility complex (MHC) antigens and failure to stimulate the proliferation of allogeneic lymphocytes.

HSC are typically available from bone marrow, Peripheral blood stem cells, Amniotic fluid, or Umbilical cord blood. In the case of a bone marrow transplant, the HSC are removed from a large bone of the donor, typically the pelvis, through a large needle that reaches the center of the bone. The technique is referred to as a bone marrow harvest and is performed under gen-eral anesthesia. Peripheral blood stem cells are a common source of stem cells for allogeneic HSCT. They can be collected from the blood through a process known as apheresis. The donors blood is withdrawn through a sterile needle in one arm and passed through a machine that removes white blood cells. The red blood cells may be returned to the donor. The peripheral stem cell yield may be boosted with daily subcutaneous injections of Granulocyte-colony stimulating factor, serving to mobilize stem cells from the donors bone marrow into the peripheral circulation.

It is also possible to extract hematopoietic stem cells from amniotic fluid. Umbilical cord blood is obtained from an infant's Umbilical Cord and Placenta after birth. Cord blood has a higher concentration of HSC than is normally found in adult blood. However, the small quantity of blood obtained from an Umbilical Cord (typically about 50 ml.) makes it more suitable for transplantation into small children than into adults. Multiple units could however be used. Newer techniques using ex-vivo expansion of cord blood units or the use of two cord blood units from different donors allow cord blood transplants to be used in adults. Cord blood can be harvested from the umbilical cord of a child being born.

Unlike other organs, bone marrow cells can be frozen (cryopreserved) for prolonged periods without damaging too many cells. This is a necessity with autologous HSC because the cells are generally harvested from the recipient months in advance of the transplant treatment. In the case of allogeneic transplants, fresh HSC are preferred in order to avoid cell loss that might occur during the freezing and thawing process. Allogeneic cord blood is typically stored frozen at a cord blood bank because it is only obtainable at the time of childbirth. To cryopre-serve HSC, a preservative, DMSO, must be added, and the cells must be cooled very slowly in a controlled-rate freezer to prevent osmotic cellular injury during ice crystal formation. HSC may be stored for years in a cryofreezer, which typically uses liquid nitrogen. In light of this, the invention may relate to typing and risk assessment of donor material already stored as described herein, before being considered for transplantation.

The invention encompasses the assessment of risk of an immune reaction, preferably a pre-transplantation risk assessment, whereby any given organ or tissue may be considered as donor material intended for transplantation. For example, kidney transplantation or renal transplantation is the organ transplant of a kidney into a patient, for example with end-stage renal disease. Kidney transplantation is typically classified as deceased-donor (formerly known as cadaveric) or living-donor transplantation depending on the source of the donor organ. Living-donor renal transplants are further characterized as genetically related (living-related) or non-related (living-unrelated) transplants, depending on whether a biological relationship exists between the donor and recipient.

Alloreactivity is defined as the reaction of a lymphocyte or antibody with an alloantigen, which may be understood as an antigen from foreign material. Alloantigen recognition may occur via direct or indirect alloantigen recognition, by which T cells may recognize alloantigens and potentially lead to transplant rejection after an organ transplant.

Graft-versus-host disease (GVHD) is a relatively common complication following an allogeneic cell, tissue or organ transplant. It is commonly associated with stem cell or bone marrow transplant but the term also applies to other forms of tissue graft or organ transplant. Immune cells (typically white blood cells) in the tissue (the graft) recognize the recipient (the host) as "foreign". The transplanted immune cells then attack the host's body cells. GVHD can also occur after a blood transfusion if the blood products used have not been irradiated.

Proteasomes are protein complexes inside all eukaryotes and archaea, and in some bacteria. In eukaryotes, they are located in the nucleus and the cytoplasm. The main function of the proteasome is to degrade unneeded or damaged proteins by proteolysis, a chemical reaction that breaks peptide bonds. Most antigenic peptides presented by MHC class I molecules result from the degradation of intracellular proteins by the proteasome. Proteasome degradation of mismatched HLA antigens can be predicted by computational tools as described herein.

FIGURES

FIG. 1: Schematic representation of peptide cleavage and binding simulation

Figure 2:
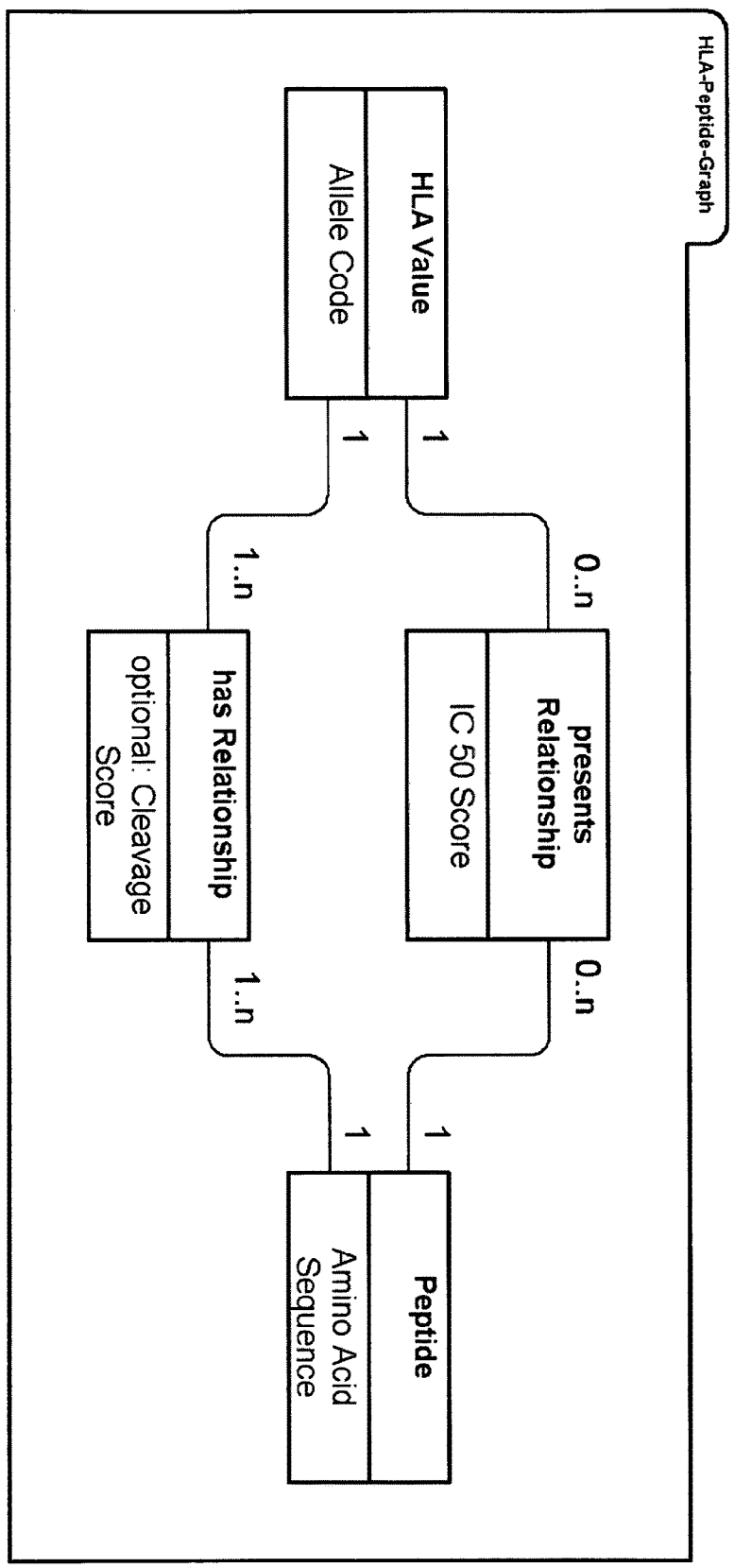

FIG. 2: Schematic of Graph data structure. From a functional perspective the core data structure for the algorithm consists of HLA Values, Peptides and relationships between those entities.

Figure 3:
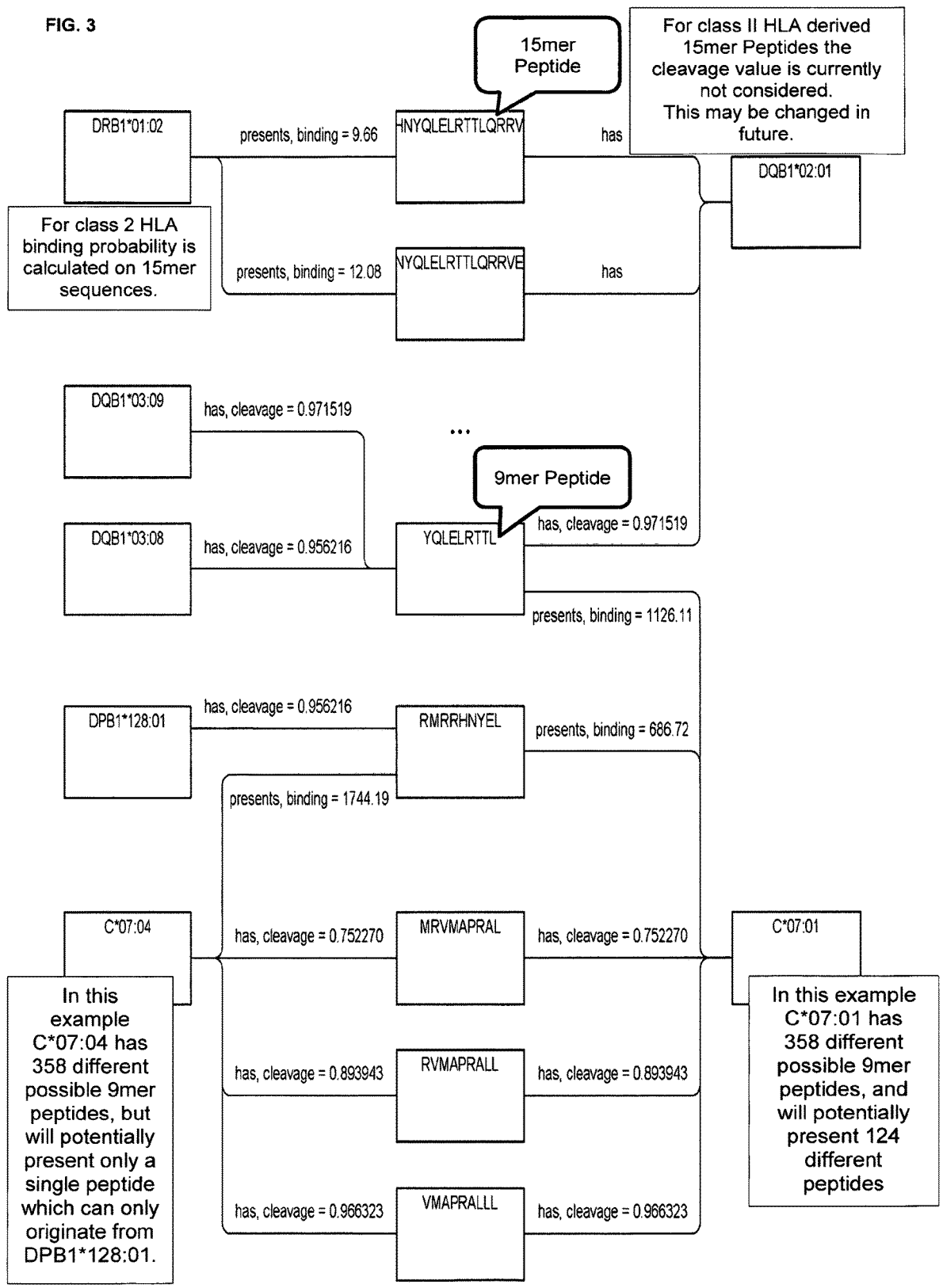

FIG. 3: Example of a graph data structure comprises nodes for peptide and HLA value entities, and "has" or "presents" relationships between said entities.

Figure 4:
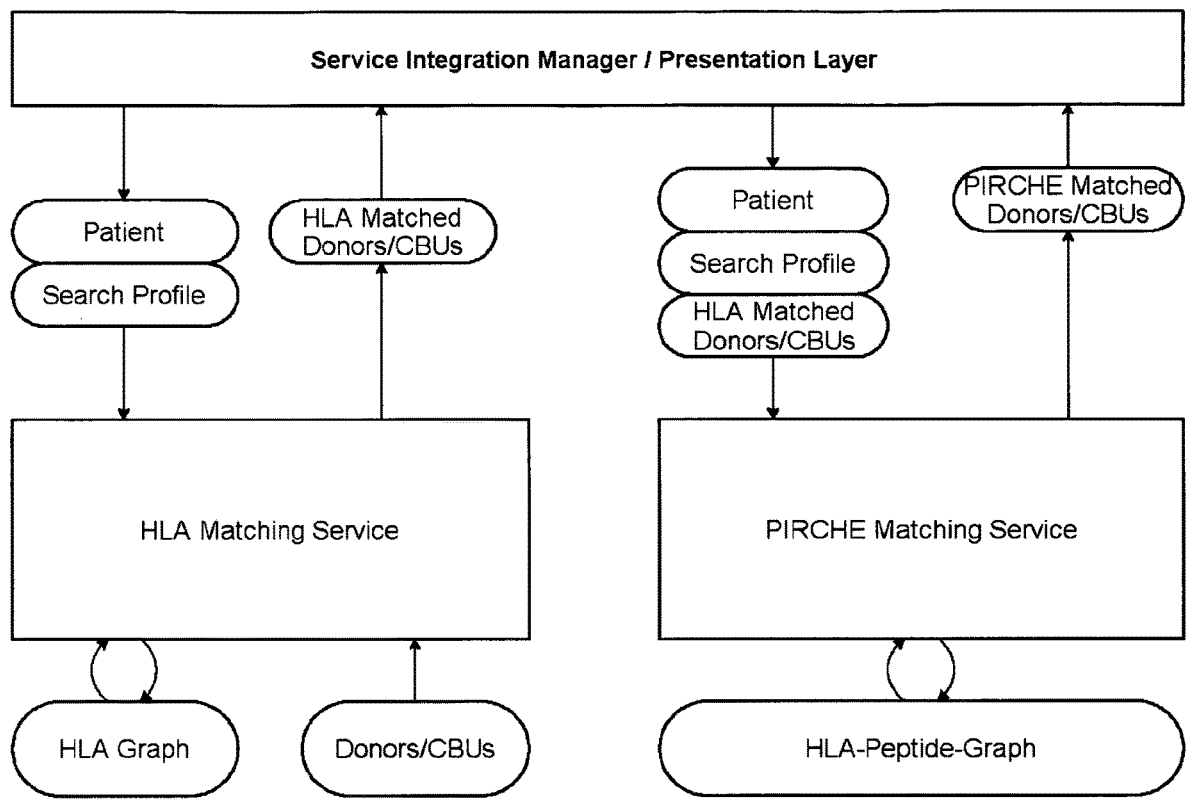

FIG. 4: Schematic representation of the combined HLA matching and PIRCHE matching software modules, preferably via a service integration manager (presentation layer).

Figure 5:
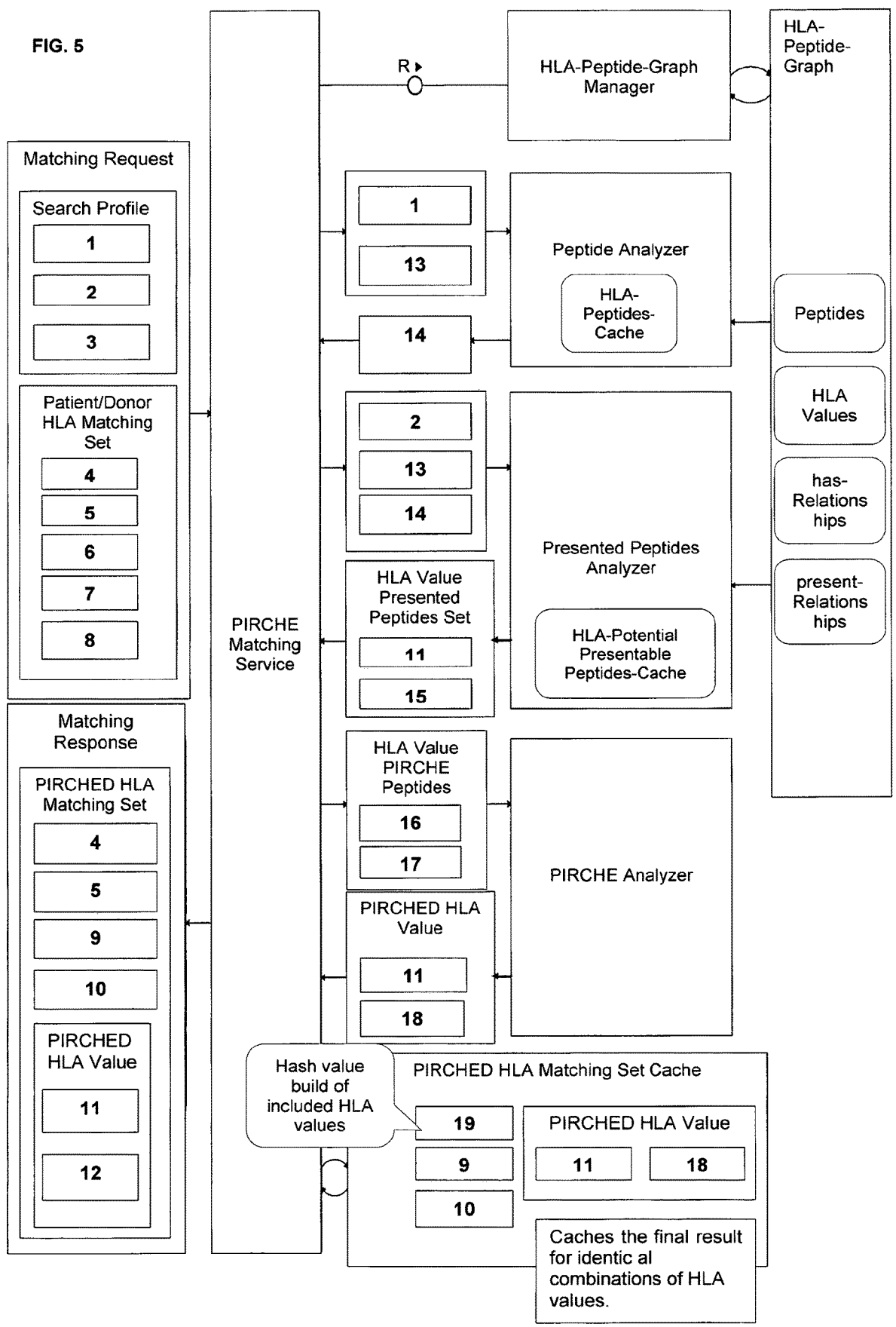

FIG. 5: provides a more detailed overview of a potential system architecture as an example.

Figure 6:
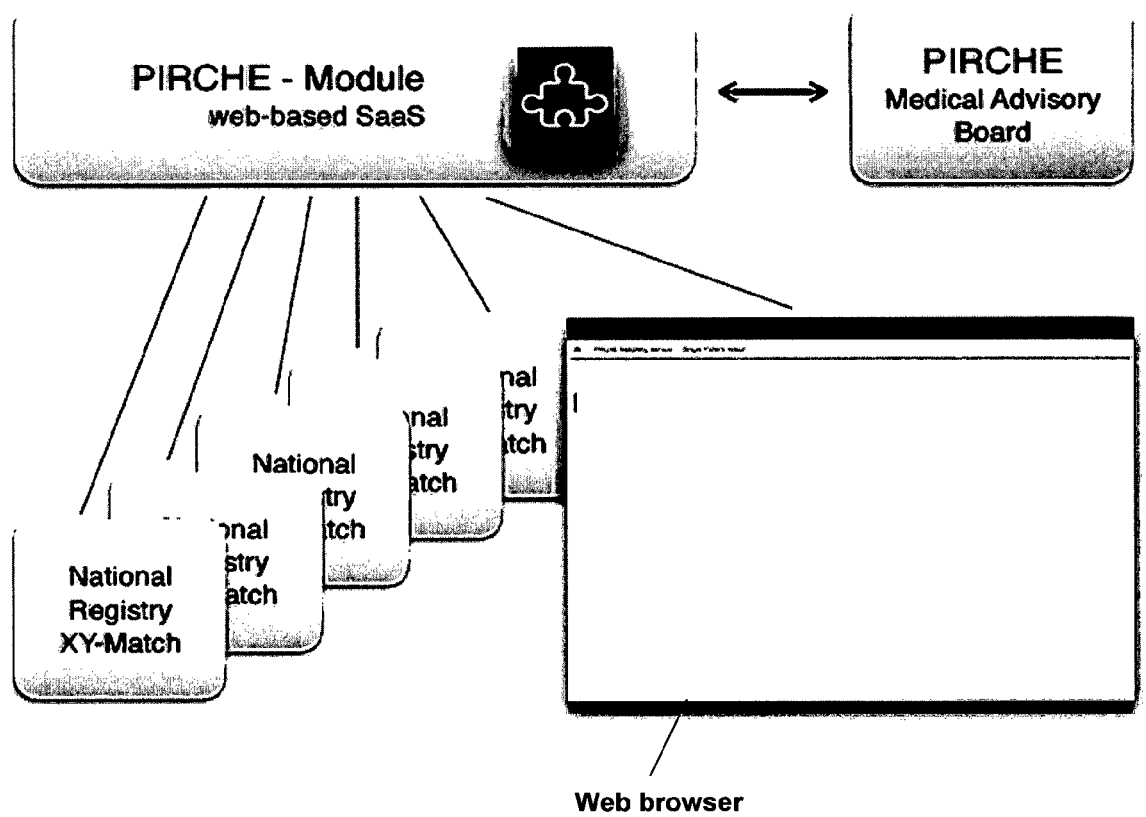

FIG. 6: provides a schematic view of the software implementation of the present invention, in particular the PIRCHE module linked with the web based SaaS, in combination with a medical advisory board.

EXAMPLES

Relevant Information for the Graph Data Structure

The graph data structure of the present invention comprises essentially all MHC class I HLA alleles and lists all possible peptides for each allele with a score value for the proteasome cleavage prediction. In one embodiment the predictions are based on the NetChop C term 3.0 prediction method. The information may comprise:

HLA-ID: ID of an HLA allele as defined in the IMGT/HLA database (accession number)
Example: HLA00005
Peptide: Peptide with a length of 5 to 15, preferably 7 to 11 or more preferably 9 amino acids. The most common length of peptides presented by MHC class I is 7-11 amino acids.
Example: MAVMAPRTL (SEQ ID NO 1)
Cleavage Score: Value ranging from 0.00-1.00 expressing the cleavage prediction for the peptide
Example score value for MAVMAPRTL (SEQ ID NO 1): 0.583079
A higher value indicates a higher cleavage probability.

The score represents a property of the relationship between a peptide and the HLA allele from which it is derived.

The data structure also contains relationships from all peptides potentially presented by any given MHC class I or class II HLA allele, in addition to the originating HLA allele that may lead to the peptide after cleavage. For each potentially presented peptide an IC 50 score representing the binding affinity is listed (preferably generated by NetMHCpan), which is considered a property of the relationship between a peptide and its likelihood of being presented by any given HLA allele.

IC 50 Score: Value ranging from 0.00-2000.00 expressing the binding affinity of the peptide
Example score value for MMVLQVSAA (SEQ ID NO 2): 285.57
A lower value indicates a higher binding affinity.

For HLA class II molecules the following information may be present:

Peptide: Peptide with a length of preferably 15 amino acids. The antigens presented by MHC class II molecules are typically longer than those presented by class I. Therefore, for the binding prediction a length of 15 amino acids is used.

Example: RAYLEGTCVDGLRRY (SEQ ID NO 3)
Score: Value ranging from 0.00-2500.00 expressing the binding affinity of the peptide
Example score value for RAYLEGTCVDGLRRY (SEQ ID NO 3): 476.80
A lower value indicates a higher binding affinity.

Outline 1: Determining PIRCHE I for MHC class I HLA:
The method as described in the following is designed to work in Graft vs. Host (GvH) direction.
Determine all recipient specific peptides that may potentially be presented by shared HLA:
Find the mismatched HLA allele between recipient and donor before initiating method, or as initial step in method, comprising for example:
  a. HLA allele matching: shared HLA
  b. HLA allele mismatch: mismatched HLA
  1. For the mismatched recipient HLA allele:
    a. Determine all peptides that have a cleavage prediction >0.5 (the threshold might be adjusted)
  2. For every shared class I HLA allele of the recipient:
    a. Check for all peptides determined in 1.a if there is a relationship with an IC50 score<500 (the threshold might be adjusted)
Determine peptides for all donor HLA values that may potentially be presented by shared HLA:
  3. For every donor HLA allele:
    a. Determine all peptides that have a cleavage prediction >0.5 (the threshold might be adjusted)
  4. For every shared class I HLA allele of the donor:
    a. Check for all peptides determined in 3.a if there is a relationship with an IC50 score <500 (the threshold might be adjusted)
Compare determined peptides of donor and recipient for each shared HLA:
  5. and 6. For every shared HLA allele:
    a. Determine all peptides presented by the recipient HLA molecule that were not determined for the corresponding donor HLA molecule Determining PIRCHE II for MHC class II HLA:
basic method is the same as for class I HLA
process all peptides independent of cleavage score
use 15mer peptides for binding prediction
Preferred embodiments:
molecular high resolution allele codes are preferably supported (e.g. A*02:01)
loci A*, B*, C*, DRB1* and DQB1* are preferably supported

PRACTICAL EXAMPLES

TABLE 1

Example of HLA-Mismatch

| Name | HLA-A | -B | -C | -DRB1 | -DQB1 |
|---|---|---|---|---|---|
| Recipient | *01:01 | *07:02 | *07:01 | *03:01 | *02:01 |
|  | *11:01 | *08:01 | *07:04 | *11:01 | *03:01 |
| Expected donor 1 (BMDW) | *01:01 | *07:02 | *07:01 | *03:01 | *02:01 |
|  | *11:01 | *08:01 | *07:02 | *11:01 | *03:01 |

Example Outline:
1. All recipient peptides of mismatched HLA (C*07:04) have to be determined (with certain thresholds).
2. For each shared HLA (A*01:01, A*11:01, . . . ) it has to be checked which of the peptides determined in 1 it can potentially present (with certain thresholds).

3. Determine all peptides of all HLA values of the donor.
4. For each shared HLA (A*01:01, A*11:01, . . . ) it has to be checked which of the peptides determined in 3 it can potentially present (with certain thresholds).
5. For each shared Class I HLA molecule: Any peptide determined in 2 that is not included in the set of peptides in 4 is a PIRCHE I.
6. For each shared Class II HLA molecule: Any peptide determined in 2 that is not included in the set of peptides in 4 is a PIRCHE II.

This means one peptide could theoretically lead to more than 1 PIRCHE as it could be presented by more than one HLA molecule.

6. For each shared Class II HLA molecule: Any peptide determined in 2 that is not included in the set of peptides in 4 is a PIRCHE II.
   Comparing the presented peptides for DRB1*03:01 between recipient and donor results in the peptide C that is only presented at the recipient. As DRB1*03:01 is a class II allele this is a PIRCHE II.

Example 2

In this example it is assumed that the allele C*07:02 may have the peptides A, H and C, i.e. the donor does now "have" the peptide "C".

TABLE 2

The table below shows examples considering only loci C* and DRB1* and is based on artificial peptide data to illustrate the concept.

| | | has Peptides | presents Peptides | presented Peptides | presented recipient specific peptides | PIRCHE I | PIRCHE II |
|---|---|---|---|---|---|---|---|
| Example 1 | | | | | | | |
| Recipient | C*07:01 | A, B | A, G, X | A, G | | | |
| | C*07:04 | A, C, J | A, F, C | /na | /na | | |
| | DRB1*02:01 | D, E | A, B | A, B | | | |
| | DRB1*03:01 | F, G | C, Y | C | C | | 1 |
| Donor | C*07:01 | A, B | A, G, X | A, G | | | |
| | C*07:02 | A, H | A, C | /na | /na | | |
| | DRB1*02:01 | D, E | A, B | A, B | | | |
| | DRB1*03:01 | F, G | C, Y | | | | |
| | | | | | PIRCHE Score | | 1 |
| Example 2 | | | | | | | |
| Recipient | C*07:01 | A, B | A, G, X | A,G | | | |
| | C*07:04 | A, C, J | A, F, C | /na | /na | | |
| | DRB1*02:01 | D, E | A, B | A, B | | | |
| | DRB1*03:01 | F, G | C, Y | C | C | | 0 |
| Donor | C*07:01 | A, B | A, G, X | A, G | | | |
| | C*07:02 | A, H, C | A, C | /na | /na | | |
| | DRB1*02:01 | D, E | A, B | A, B | | | |
| | DRB1*03:01 | F, G | C, Y | C | C | | |
| | | | | | PIRCHE Score | | 0 |

Example 1

1. All recipient peptides of mismatched HLA (C*07:04) have to be determined (with certain thresholds).
   The recipient "has" the peptides A, B, C, J, D, E, F, G.
2. For each shared HLA it has to be checked which of the peptides determined in 1 it can potentially present (with certain thresholds).
   The HLA molecule for DRB1*03:01 can potentially present the peptides C and Y. As the donor does not "have" Y the HLA molecule can actually only present C. For the mismatched HLA molecule the presented peptides are not relevant.
3. Determine all peptides of all HLA values of the donor.
   The donor "has" the peptides A, B, H, D, E, F, G.
4. For each shared HLA it has to be checked which of the peptides determined in 3 it can potentially present (with certain thresholds).
   The HLA molecule for DRB1*03:01 can potentially present the peptides C and Y. As the donor does not "have" C or Y the HLA molecule can actually not present any of the peptides. For the mismatched HLA molecule the presented peptides are not relevant.
5. For each shared Class I HLA molecule: Any peptide determined in 2 that is not included in the set of peptides in 4 is a PIRCHE I.

DRB1*03:01 HLA molecules can potentially present C peptides.
Comparing the presented peptides for DRB1*03:01 between recipient and donor results in all the peptides of the recipient being presented by the donor, too. Therefore, there is no PIRCHE for DRB1*03:01.

Data Structure

From a functional perspective the core graph data structure for the algorithm consists of HLA Values, Peptides and relationships between those entities (see FIG. 2).

An HLA Value "has" a number of Peptides, meaning the proteasome cleavage of the amino acid sequence of the HLA Value may potentially result in the related Peptides. The likelihood of this cleavage is expressed by the Cleavage Score for class I HLA. For class II HLA cleavage this values is preferably not maintained, as cleavage patterns may not be well defined yet.

Furthermore, an HLA value may "present" a number of Peptides, meaning the Peptide may be bound to and presented by the HLA molecule on the cell surface. The IC 50 score expresses the likelihood of the actual binding of a Peptide to an HLA molecule. The IC 50 score is defined for relationships to class I and class II HLA Values.

Preferably, Peptides with a sequence of 9 amino acids are used as potentially presented Peptides by class I HLA and Peptides with a sequence of 15 amino acids are used as potentially presented Peptides by class II HLA. However, other Peptide length may be included in subsequent releases.

The graph data structure provides HLA Value entities, Peptide entities and relationships between those entities. The structure comprises all relevant peptides and the corresponding cleavage scores for all relevant HLA value entities, including Class I and Class II Binding Predictions.

The graphic in FIG. 3 depicts an example segment of this data graph. This data structure can ideally be stored in a graph database in the form shown in the graphics above. Alternatively, suitable storage concepts include storage in key value stores and storage in relational data base tables.

As shown in the example of FIG. 3, the abstraction of the real world entities in a graph structured data model is ideally reflecting the biological background. Therefore, for the actual storage of the data in the system a graph database is preferred. Entities are stored as unique nodes, thereby enabling efficient processing of data.

Key value stores offer performant look up of data while not being optimal in terms of size as entities may have to be stored redundantly. This concept represents one embodiment of the invention, in particular if performance becomes a problem and is ideal for caching.

Relational database management systems are optimized for aggregating data and also offer ideal storage but will need frequent join operations on large data tables. This might have a negative impact on performance.

A graph data base is optimized for highly connected data and allows a high performance access to relationships in combination with an ideal minimized storage size. Furthermore, when the biological background factors to be considered in the matching method described herein are extended and the domain model becomes more complex, the graph structure will allow ideal integration of such extensions.

The following scales should be considered:
Peptides: ~3.000.000 (~1.832.000 9 mer peptides+15mer peptides)
HLA Values: ~10.000
Relationships: ~10.000*1000

It is sufficient, and preferred, to only include those Peptides in the graph structure that can potentially be presented by at least one HLA molecule.

System Architecture

FIG. 4 discloses a schematic representation of the combined HLA matching and PIRCHE matching software modules, preferably via a service integration manager (presentation layer).

The PIRCHE Matching module is designed as a service component that can be integrated into other applications. This allows offering the PIRCHE Matching Service as a standalone service as well as integration into existing applications, like HLA Matching systems.

As the PIRCHE Matching Service needs to be provided with identified HLA matches and mismatches between patients and donors integration into an existing HLA Matching system is an ideal combination.

As the PIRCHE Matching Service prefers high resolution typed HLA allele values and these are often not available for many donors a high resolution HLA genotype estimation service is another service integration that leads to a more sophisticated solution.

The combination of HLA Matching Services, high resolution HLA genotype estimation services and the PIRCHE Matching Service offers new possibilities like the applicability of the solution to large registries of not high resolution typed donors, the integration of the results of all services into a scoring system to rank donors according to HLA matching, high resolution HLA estimation, PIRCHEs and other factors like cell count, blood group, infectious diseases markers, gender and age in combination. For a search coordinator or physician this will allow the identification of better HSCT donors in shorter time leading to better treatment outcomes.

The PIRCHE Matching Service accepts molecular high resolution patient HLA data, a search profile and a list of molecular high resolution HLA values, e.g. of matched donors or CBUs, i.e. the matching and mismatching HLA values have to be identified.

Based on the HLA-Peptide-Graph the HLA-Peptide-Matching algorithm analyses the PIRCHE I and PIRCHE II values of each donor/CBU and returns the given Donors/CBUs list enriched with the PIRCHE information to the service client.

To integrate the service into another system it is preferred to have a superior Service Integration Manager Component that is the service client and orchestrates it with other services like the HLA Matching Service and the high resolution HLA genotype estimation services to provide a comprehensive solution.

FIG. 5 provides a more detailed overview of potential system architecture as an example.

The graphic in FIG. 5 describes the PIRCHE Matching Service Component in more detail. The Matching Service consists of the Main Service Layer and several sub components, the most important being the Peptide Analyzer, the Presented Peptides Analyzer, the PIRCHE Analyzer and the HLA-Peptide-Graph Manager. Furthermore, it consists of the HLA-Peptide-Graph store and a number of caches to improve performance.

The PIRCHE Matching Service is called by the client with a Matching Request data structure and provides a Matching Response data structure as the result.

The Matching Request data structure consists of a Search Profile and set of Patient/Donor HLA Matching Sets. The Search Profile specifies the Cleavage Threshold, the IC 50 Score Threshold for the peptide binding affinity and the requested Matching Direction (Graft vs. Host or Host vs. Graft).

A Patient/Donor HLA Matching Set contains the HLA Matching result of a patient and a donor. I.e. it contains the shared and the mismatched HLA values between patient and donor. As the mismatches are dependent on the patient donor combination this has to be provided for each donor to be analyzed. In addition, it contains the ID of the patient and the ID of the donor for identification purposes.

The Matching Response contains PIRCHED HLA Matching Sets. Each set comprises a set of PIRCHED HLA Values, each consisting of the HLA Value and the corresponding number of PIRCHE I or PIRCHE II that was determined. Additionally, the PIRCHED HLA Matching Sets contain the total number of PIRCHE I or PIRCHE II for the considered HLA loci and the ID of the patient as well as the ID of the donor for identification purposes.

Internally the system may be made up of the following sub components:
The HLA-Peptide-Graph Manager is responsible for creating and updating the HLA-Peptide-Graph.
The Peptide Analyzer is determining the HLA derived peptides based on the HLA-Peptide-Graph for a given set of HLA values with an optional cleavage threshold.
The Presented Peptides Analyzer is determining which peptides of a given set are potentially being presented on a set of given HLA molecules with a given IC 50 Score Threshold based on the HLA-Peptide-Graph.

The result consists of a set of potentially presented peptides for every given HLA value.

The PIRCHE Analyzer takes HLA values and corresponding sets of patient and donor presented peptides and determines for every HLA value the number of PIRCHE I or PIRCHE II.

Main Use Case of combined HLA match/PIRCHE system
1. User logs into HLA Match/PIRCHE system
2. User creates a new patient
3. User enters patient HLA
4. User navigates to Search
5. User configures search profile and starts search
6. System performs search with search profile settings
7. System shows Search Result Screen
8. User can switch between CBU result list and donor result list
9. User exports donors as csv file (optional)

In a preferred embodiment it is possible to display a donor search result and to switch between CBU and donor search result.

Donor Type Search

The solution will comprise a donor genotype database on which the PIRCHE Matching Service can be executed for a given patient to determine a list of potential donor types that have a genotype with permissible mismatches.

| Donor Type ID | Score | HvG | GvH | A* | B* | C* | DRB1* | DQB1* | PIRCHE I | PIRCHE II | Frequency |
|---|---|---|---|---|---|---|---|---|---|---|---|

The columns of the Donor Search Result Screen are:
Donor Type ID
Score (For first release: PIRCHE I+PIRCHE II, may be extended later)
HvG (Host vs Graft mismatches)
GvH (Graft vs Host mismatches)
A*
B*
C*
DRB1*
DQB1*
PIRCHE I
PIRCHE II
Frequency (Frequency of this donor genotype based on the haplotype frequencies used to create the donor genotype database)
(Ethnicities of Donor Types will be added in subsequent releases)

The donor genotype database will allow searching for donor genotypes with permissible mismatches. A typical search in an existing donor registry of real donors might lead to not realizing a 10/10 matched donor genotype at all, for example if such a donor is not present in the searched registry. By searching the donor genotype database with HLA and PIRCHE Matching, genotype search templates may be determined that allow to steer further searches in the right direction, e.g. by identifying donor types that should be frequent in certain registries, e.g. because of gender, sex, ethnicity, etc.

The PIRCHE Matching Module can also be used to match real CBUs and donors. The user can switch between the result lists of the CBU inventory, the real donor inventory and the donor genotype database.

HLA Graph-Database Improved PIRCHE Speed

For validation purposes an artificial test file of patients and accompanied donors was generated. This file contains 26.000 pairs of theoretical patients & donors of hematopoietic stem cells with 1 mismatch in a 10 out of 10 HLA typing as well as PIRCHE I+II values generated by each pair.

The construction principle is as follows. Patient and donor have 1 serological mismatch in HLA-A locus. This mismatch is fixed in position and the kind of allele throughout all following pairs. The following patient & donor pairs vary by permutation of all existing alleles of the HLA loci HLA-A, HLA-B, HLA-C, HLA-DRB1, and HLA-DQB1 simultaneously at the site of the patient and donor. The permutation of the matched or shared alleles leads to different PIRCHE values even for this single fix mismatch in each of the pairs.

This file was used to validate the correctness of the algorithm transfer from an earlier Perl Script implementation into the new HLA Graph database structure. Correctness was given when all PIRCHE values where the same in the original Perl Script as well as in the Graph database.

The original implementation needed 11 hours to perform the calculation for all 26,000 pairs. The implementation described herein using the graph data structure took only 10 seconds to perform all 26,000 PIRCHE calculations.

The speed improvement together with the web browser based user interface now allows an interactive use of the algorithm. Now clinical working situations of 1 patient with 10 to 100 potential donors run in parts of a second. The patient can be tested very quickly with different pools of potential donors. e.g. coming from different registries or different countries. No waiting necessary, answers come immediately and are available everywhere where a web browser provides access to the internet.

The graph data structure therefore provides not only improved speed in computing. Due to the biological context of the data structure, the biological samples represented in the data (not directly, but assuming the data corresponds indirectly to patient samples) and ultimately the improved speed of identifying permissible mismatched HLA donor material, the invention provides unexpected technical effects and benefits. Until present, earlier methods of matching and selection of permissible mismatched HLA donor material were slow and limited by both the biological approaches applied (i. e. searching only for 10/10 matches) and the relatively inefficient computing approaches applied previously.

The present invention is therefore defined by a combination of novel features regarding the biological context and mechanism employed to identify permissible mismatches (indirect presentation vs direct presentation), in addition to the novel data structure employed for speedier processing. The combination of these features leads to unexpected synergy, resulting in much faster processing times and therefore entirely novel approaches towards interrogating multiple stem cell or donor tissue databases and registers from around the world in search efforts to find permissible donor material.

Software Implementation

The system described herein was incorporated into an intuitive visual browser interphase enabling access to the underlying HLA Graph-database. The visual interface also lead to improved PIRCHE speed and enables a more interactive working style during donor material search. Previous attempts at HLA matching and similar search engines are severely limited by their slow processing times. According to some early systems, the results to particular inquiries would be provided first one or more days after requests had been sent.

The graph database structure enables a reduction in test file runtime from 11 h down to 10 sec ($\approx$26.000 patient/donor pairs).

The software implantation of the system incorporates a Software as a Service (SaaS) Json—REST interface that allows PIRCHE integration into any given existing donor selection system already existing. The invention (data structure and interrogation thereof) may therefore itself be represented as a module that is capable of integration with other HLA matching services.

The invention claimed is:

1. A computer-implemented method for determining numbers of predicted indirectly recognized HLA epitopes (PIRCHES) between:

one or more donors and one or more recipients of transplantation material, wherein donor-recipient pairs are formed by either multiple of the one or more donors with one recipient, or multiple of the one or more recipients with one donor, wherein said PIRCHES are
  i) recipient- or donor-specific HLA-derived peptides from a mismatched recipient-HLA allele, or
  ii) donor-specific HLA-derived peptides from a mismatched donor-HLA allele, and are predicted to be presented by an HLA molecule, wherein the method comprises:

a) identifying peptides from HLA molecules of i) the one recipient or ii) the one donor, wherein said peptides are identified by the computer-implemented method which is configured to predict cleavage sites of a human proteasome within said mismatched HLA molecules;

b) determining the peptides identified in a) that are predicted to be presented by one or more HLA molecules, wherein said peptides are determined by the computer-implemented method which is further configured to predict presentation of a peptide by one or more HLA molecules via predicting binding of the peptide to the one or more HLA molecules;

c) identifying peptides from the HLA molecules of i) the one donor or ii) the one recipient, respectively, by the computer-implemented method of a);

d) determining the peptides identified in c) that are predicted to be presented by the one or more HLA molecules by the computer-implemented method of b), to define a set of peptides;

wherein e) for each MHC Class I HLA molecule, any peptide determined in b) that is not included in the set of peptides in d) is a mismatched HLA peptide and is characterized as PIRCHE I, or for each MHC Class II HLA molecule, any peptide determined in b) that is not included in the set of peptides in d) is a mismatched HLA peptide and is characterized as a PIRCHE II, wherein f) a) to d) are performed based on information stored in a graph data structure, wherein one or more nodes of the graph data structure are HLA value entities comprising an informational and/or computational representation of the HLA molecules, one or more nodes of the graph data structure are peptide entities comprising an informational and/or computational representation of the peptides, and edges between HLA value entities and peptide entities represent relationships between the HLA molecules and the peptides, and wherein a first relationship between a HLA value entity and a peptide entity represents a likelihood that the proteasome cleavage of the HLA molecule represented by the HLA value entity yields the peptide represented by the peptide entity, wherein the likelihood of proteasome cleavage to yield the peptide is expressed by a cleavage probability score between 0 and 1 and the peptide is identified under a) when the cleavage probability score is ≥0.5, and a second relationship between a HLA value entity and a peptide entity represents a likelihood that the peptide represented by the peptide entity binds to the HLA molecule represented by the HLA value entity, wherein the likelihood of peptide binding is expressed by an $IC_{50}$ score and the peptide is determined under b) when the $IC_{50}$ score is ≤500 nM for PIRCHE I or ≤1000 nM for PIRCHE II; and determining the numbers of the PIRCHES, and based thereon, selecting the donor-recipient pair for transplantation that has the lowest number of PIRCHE-I and/or PIRCHE II, further comprising transplanting the transplantation material from the donor to the recipient of the selected donor-recipient pair.

2. The method of claim 1, wherein a search profile for the one recipient or the one donor is provided by a requestor via a matching request to a PIRCHE matching service and results comprising data of the PIRCHE donor-recipient pair that has been selected for the transplantation of biological material is provided to the requestor via a matching response.

3. The method of claim 1, wherein f) is carried out by one or more software modules.

4. The method of claim 1, wherein the method is preceded by HLA matching between the donor and the recipient.

5. The method of claim 1, wherein the selected HLA molecules are HLA loci A*, B*, C*, DRB1* and DQB1*, and optionally DPB1* and DRB3/4/5*.

6. The method of claim 1, wherein the information corresponding to donor HLA value entities is obtained from one or more donor profiles.

7. The method of claim 1, wherein the donor profiles are stored in an additional data structure, database, library and/or simulation of the peptide and/or HLA value entities of any given one or more theoretical or virtual donors.

8. The method of claim 1, wherein multiple donor profiles or donor types are stored in a donor data structure, database, library and/or simulation comprising essentially all possible donors for essentially all possible genotypes or possible combinations of HLA alleles and/or haplotypes.

9. The method of claim 1, wherein said method comprises searching by a client, via a matching request, with recipient information corresponding to a biological recipient in need of a transplantation against one or more donor profiles, wherein the result (outcome) provides information on the one or more best-matched mismatched donor profiles to said client via a matching response.

10. The method of claim 8, wherein the one or more best-matched mismatched donor profiles are 9/10 mismatched donors with a lowest possible number of PIRCHES compared to other mismatched donors.

11. The method of claim 8, wherein a software module for executing said method is functionally connected to electronic registers of donor material, wherein the method comprises sending a query from an end-user to said register for any given one or more best-matched mismatched donor material corresponding to the data of the donor-recipient pair selected for transplantation of biological material.

12. The method of claim 1, wherein information representing the frequency of any given combination of HLA alleles (haplotype or genotype) in any one or more human populations is incorporated in the donor profile.

13. The method of claim 11, wherein electronically stored HLA typing data for donor material typed with "low-" or "medium-" resolution HLA typing is converted via a computer-implemented method into a "high-" resolution-similar or analogous HLA typing status on the basis of the known population frequencies of any given combination of HLA alleles determined by said with "low-" or "medium-" resolution HLA typing, thereby enabling interrogation of HLA typing data previously obtained via "low-" or "medium-" resolution techniques using the method and/or system as described herein.

14. The method of claim 1, comprising a) conversion of HLA typing data from "low-" or "medium-" resolution HLA typing to "high-" resolution data, b) HLA matching of said donor information with recipient HLA information and c) PIRCHE matching according to the method.

15. System for selecting and/or screening donor material for transplantation, for example for selecting donor material with permissible mismatches from mismatched unrelated donors, comprising software modules for HLA matching, and PIRCHE matching according to the method of claim 1.

16. The system of claim 15, wherein said HLA software module carries out HLA matching between donor and recipient HLA typing data on the basis of high resolution allele coding and wherein said PIRCHE matching incorporates the HLA matching information generated by said HLA matching software module, such that the PIRCHE matching module accepts a patient, a matching profile and list of HLA matched donors and returns the input donor list enriched with the PIRCHE information as an output.

17. The system of claim 15, wherein patient information and search profiles are provided via a shared service integration manager software module, wherein said shared service integration manager module is connected to both HLA matching and PIRCHE matching modules, such that patient information and search profiles are initially processed by said HLA matching software module, which subsequently provides a patient, a matching profile and list of HLA matched donors via said shared manager module for analysis of PIRCHE numbers to said PIRCHE matching module.

* * * * *

UNITED STATES PATENT AND TRADEMARK OFFICE
CERTIFICATE OF CORRECTION

PATENT NO. : 10,726,941 B2
APPLICATION NO. : 15/309211
DATED : July 28, 2020
INVENTOR(S) : Ralf Schliehe-Diecks and Hendrikus Theodorus Spierings It is certified that error appears in the above-identified patent and that said Letters Patent is hereby corrected as shown below:

In the Specification

In Column 5, Line 14, please delete "1050" and insert -- IC50 --, therefore.

In Column 5, Line 15, please delete "1050" and insert -- IC50 --, therefore.

In Column 7, Line 33, please delete "5500" and insert -- ≤500 --, therefore.

In Column 7, Line 31, please delete "51000" and insert -- ≤ 1000 --, therefore.

Signed and Sealed this
Eighth Day of December, 2020

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 9
<212> TYPE: PRT
<213> ORGANISM: Homo sapiens

<400> SEQUENCE: 1

Met Ala Val Met Ala Pro Arg Thr Leu
1               5

<210> SEQ ID NO 2
<211> LENGTH: 9
<212> TYPE: PRT
<213> ORGANISM: Homo sapiens

<400> SEQUENCE: 2

Met Met Val Leu Gln Val Ser Ala Ala
1               5

<210> SEQ ID NO 3
<211> LENGTH: 15
<212> TYPE: PRT
<213> ORGANISM: Homo sapiens

<400> SEQUENCE: 3

Arg Ala Tyr Leu Glu Gly Thr Cys Val Asp Gly Leu Arg Arg Tyr
1               5                   10                  15

<210> SEQ ID NO 4
<211> LENGTH: 15
<212> TYPE: PRT
<213> ORGANISM: Homo sapiens

<400> SEQUENCE: 4

His Asn Tyr Gln Leu Glu Leu Arg Thr Thr Leu Gln Arg Arg Val
1               5                   10                  15

<210> SEQ ID NO 5
<211> LENGTH: 15
<212> TYPE: PRT
<213> ORGANISM: Homo sapiens

<400> SEQUENCE: 5

Asn Tyr Gln Leu Glu Leu Arg Thr Thr Leu Gln Arg Arg Val Glu
1               5                   10                  15

<210> SEQ ID NO 6
<211> LENGTH: 9
<212> TYPE: PRT
<213> ORGANISM: Homo sapiens

<400> SEQUENCE: 6
```

```
Tyr Gln Leu Glu Leu Arg Thr Thr Leu
1               5

<210> SEQ ID NO 7
<211> LENGTH: 9
<212> TYPE: PRT
<213> ORGANISM: Homo sapiens

<400> SEQUENCE: 7

Arg Met Arg Arg His Asn Tyr Glu Leu
1               5

<210> SEQ ID NO 8
<211> LENGTH: 9
<212> TYPE: PRT
<213> ORGANISM: Homo sapiens

<400> SEQUENCE: 8

Met Arg Val Met Ala Pro Arg Ala Leu
1               5

<210> SEQ ID NO 9
<211> LENGTH: 9
<212> TYPE: PRT
<213> ORGANISM: Homo sapiens

<400> SEQUENCE: 9

Arg Val Met Ala Pro Arg Ala Leu Leu
1               5

<210> SEQ ID NO 10
<211> LENGTH: 9
<212> TYPE: PRT
<213> ORGANISM: Homo sapiens

<400> SEQUENCE: 10

Val Met Ala Pro Arg Ala Leu Leu Leu
1               5
```